United States Patent
Chou et al.

(10) Patent No.: US 12,264,166 B2
(45) Date of Patent: Apr. 1, 2025

(54) ASYMMETRIC FUSED AROMATIC RING DERIVATIVE CONTAINING SULFONYL GROUP, HYDROGEN PRODUCTION DEVICE AND OPTOELECTRONIC COMPONENT

(71) Applicant: National Tsing Hua University, Hsinchu (TW)

(72) Inventors: Ho-Hsiu Chou, Hsinchu (TW); Wei-Cheng Lin, Hsinchu (TW); Yuan-Ting Tseng, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 0 days.

(21) Appl. No.: 17/864,723

(22) Filed: Jul. 14, 2022

(65) Prior Publication Data
US 2023/0227475 A1    Jul. 20, 2023

(30) Foreign Application Priority Data
Jan. 20, 2022 (TW) ................... 111102361

(51) Int. Cl.
C07D 519/00 (2006.01)
B01J 31/02 (2006.01)
H10K 85/60 (2023.01)

(52) U.S. Cl.
CPC .......... *C07D 519/00* (2013.01); *B01J 31/022* (2013.01); *H10K 85/6576* (2023.02)

(58) Field of Classification Search
None
See application file for complete search history.

(56) References Cited

FOREIGN PATENT DOCUMENTS

| | | |
|---|---|---|
| CN | 101945878 A | 1/2011 |
| JP | 2007269775 A | 10/2007 |

OTHER PUBLICATIONS

Lin et al., "Sulfide oxidation tuning in 4,8-bis(5-(2-ethylhexyl)thiophen-2-yl)benzo[1,2-b:4,5-b']dithiophene based dual acceptor copolymers for highly efficient photocatalytic hydrogen evolution", Journal of Materials Chemistry A, 2022, pp. 6641-6648, vol. 10.

*Primary Examiner* — Noble E Jarrell
(74) *Attorney, Agent, or Firm* — The Webb Law Firm

(57) ABSTRACT

An asymmetric fused aromatic ring derivative containing sulfonyl group, which includes a structure represented by formula (I). Formula (I) is defined as in the specification. A use of the asymmetric fused aromatic ring derivative containing sulfonyl group, which is used as a photocatalyst. A hydrogen production device, which includes the asymmetric fused aromatic ring derivative containing sulfonyl group. An optoelectronic component, which includes the asymmetric fused aromatic ring derivative containing sulfonyl group.

9 Claims, 14 Drawing Sheets

ASYMMETRIC FUSED AROMATIC RING DERIVATIVE CONTAINING SULFONYL GROUP, HYDROGEN PRODUCTION DEVICE AND OPTOELECTRONIC COMPONENT

CROSS-REFERENCE TO RELATED APPLICATION

This application claims priority to Taiwanese Application Number 111102361, filed Jan. 20, 2022, the disclosure of which is hereby incorporated by reference in its entirety.

BACKGROUND OF THE INVENTION

Field of the Invention

The present disclosure relates to an organic conjugated molecule, a use thereof, a hydrogen production device and an optoelectronic component. More particularly, the present disclosure relates to an asymmetric fused aromatic ring derivative containing sulfonyl group, a use thereof, a hydrogen production device and an optoelectronic component.

Description of Related Art

With the rapid development of social economy and the increase of population, the traditional non-renewable resources such as oil, natural gas and coal are being consumed at an extremely fast rate. The problem of the resource shortage has become one of the major problems in the world today. Therefore, the development and the use of green and sustainable new energy sources have become very important. The common hydrogen production methods include hydrolysis method, coal gasification method, petroleum cracking and photocatalytic water splitting, etc. The photocatalytic water splitting uses solar energy to decompose water to generate hydrogen, which has the advantages of low cost and no secondary pollution. It is a recyclable hydrogen production technology. Furthermore, there are also having the solar cell that convert electrical energy into chemical energy, and using the solar cell as a source of electrical energy to perform photoelectric conversion reaction to generate hydrogen.

In the recent years, the organic conjugated molecule as the photocatalyst has been developed rapidly because of their potential advantages, such as tunable optical and electronic properties, low-cost fabrication and flexible molecular structure. However, the efficiency of materials on the market still cannot reach the level of industrialization currently.

Therefore, how to synthesize the high-efficiency material, so that it has good hydrogen production efficiency to achieve the level of industrialization, which is the goal of the relevant scholars and industry.

SUMMARY OF THE INVENTION

According to one aspect of the present disclosure, an asymmetric fused aromatic ring derivative containing sulfonyl group is provided. The asymmetric fused aromatic ring derivative containing sulfonyl group includes a structure represented by formula (I):

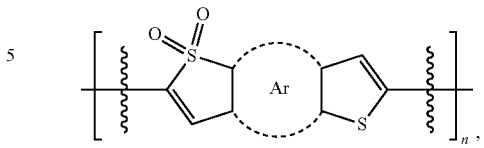

formula (I)

wherein each wavy lines independently indicates to connect with a monomer unit, and the monomer unit is connected to the structure represented by formula (I) by a metal-catalyzed coupling method, Ar is an aromatic ring compound, and n is an integer from 1 to 100.

According to another aspect of the present disclosure, a use of the asymmetric fused aromatic ring derivative containing sulfonyl group according to the aforementioned aspect is provided, which is used as a photocatalyst.

According to further another aspect of the present disclosure, a hydrogen production device is provided. The hydrogen production device includes a solution system. The solution system includes the asymmetric fused aromatic ring derivative containing sulfonyl group according to the aforementioned aspect and water.

According to still another aspect of the present disclosure, an optoelectronic component is provided. The optoelectronic component includes the asymmetric fused aromatic ring derivative containing sulfonyl group according to the aforementioned aspect.

BRIEF DESCRIPTION OF THE DRAWINGS

The present disclosure can be more fully understood by reading the following detailed description of the embodiment, with reference made to the accompanying drawings as follows.

DESCRIPTION OF THE INVENTION

Figure 1:
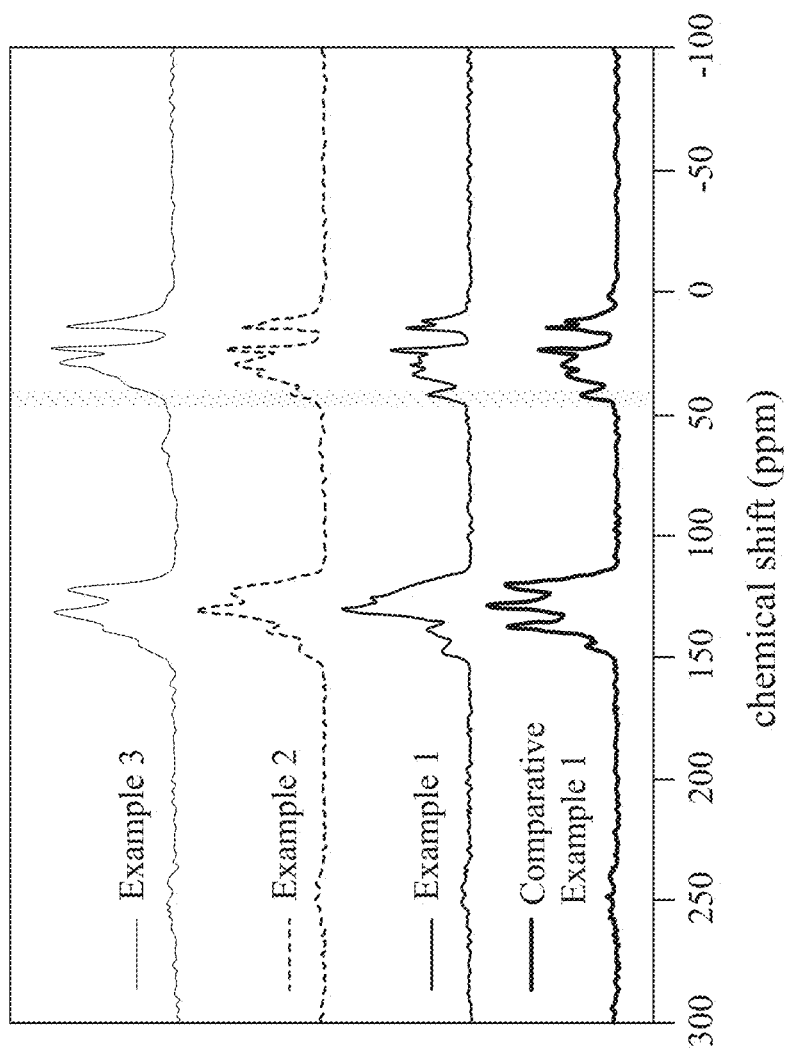
FIG. 1 is a $^{13}C$ NMR spectrum of Example 1 to Example 3 and Comparative Example 1.

The present disclosure will be further exemplified by the following specific embodiments. However, the embodiments can be applied to various inventive concepts and can be embodied in various specific ranges. The specific embodiments are only for the purposes of description, and are not limited to these practical details thereof.

In the present disclosure, the compound structure can be represented by a skeleton formula, and the representation can omit the carbon atom, the hydrogen atom and the carbon-hydrogen bond. In the case that the functional group is depicted clearly in the structural formula, the depicted one is preferred.

In the present disclosure, if a group is not indicated specifically which is substituted or not, the group can be represented the substituted or unsubstituted group. For example, "alkyl group" can be represented the substituted or unsubstituted alkyl group.

Asymmetric Fused Aromatic Ring Derivative Containing Sulfonyl Group

An asymmetric fused aromatic ring derivative containing sulfonyl group of the present disclosure, which includes a structure represented by formula (I):

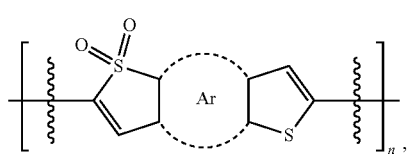

formula (I)

wherein each wavy line independently indicates to connect with a monomer unit, and the monomer unit is connected to the structure represented by formula (I) by a metal-catalyzed coupling method, Ar is an aromatic ring compound, and n is an integer from 1 to 100.

Specifically, the donor-acceptor type (D-A) conjugated polymer of the previously research has achieved excellent photocatalytic hydrogen evolution efficiency, and the generated push-pull system can narrow the bandgap of the polymer to enhance the harvesting of solar energy and separate photoinduced exciton efficiently. However, this type of the conjugated polymer will limit the numbers of electron-withdrawing group, such as a sulfonyl group, so that larger than 50% of the units in the conjugated polymer are not the electron-output sites.

Therefore, the asymmetric fused aromatic ring derivative containing sulfonyl group represented by formula (I) of the present disclosure is synthesized, which can be used as a dual-acceptor type (A1-A2) conjugated polymer. The incorporation of acceptor unit containing the sulfonyl group into the main chain of the polymer, the wettability of the conjugated polymer can be enhanced through the interaction of the OH group and water in the chain and between the chains. Furthermore, the sulfonyl group also has the abundant electron-output sites, which can transfer electrons to the co-catalyst, and the conjugated polymer can have the better thermal stability and hydrogen evolution effect by the modification of asymmetric structure.

In detail, the aforementioned Ar can be but not limited to a structure represented by formula (i-1), formula (i-2), formula (i-3) or formula (i-4):

formula (i-1)

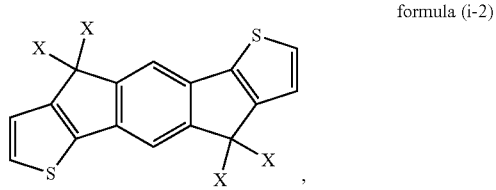

formula (i-2)

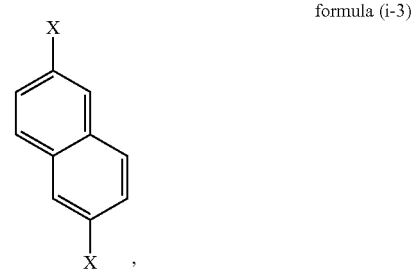

formula (i-3)

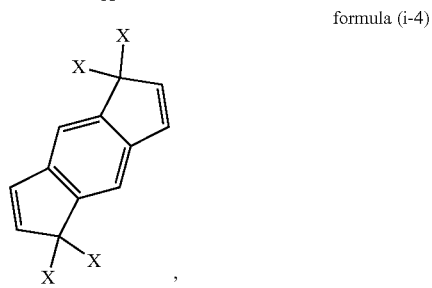

formula (i-4)

wherein each X is independently an organic ring, which is substituted or unsubstituted, or an alkyl group with linear, branched or cyclic of 1 to 30 carbon atoms.

Furthermore, the aforementioned metal-catalyzed coupling method can be Suzuki-Miyaura coupling method, Stille coupling method or direct arylation coupling method, and the aforementioned monomer unit can include a structure represented by formula (ii-1), formula (ii-2), formula (ii-3), formula (ii-4), formula (ii-5), formula (ii-6), formula (ii-7), formula (ii-8), formula (ii-9), formula (ii-10), formula (ii-11), formula (ii-12), formula (ii-13), formula (ii-14), formula (ii-15), formula (ii-16), formula (ii-17), formula (ii-18), formula (ii-19), formula (ii-20), formula (ii-21), formula (ii-22), formula (ii-23), formula (ii-24), formula (ii-25), formula (ii-26), formula (ii-27), formula (ii-28), formula (ii-29), formula (ii-30), formula (ii-31) or formula (ii-32):

formula (ii-1)
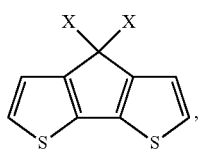
formula (ii-2)
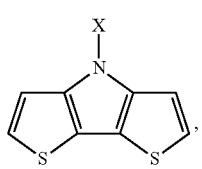
formula (ii-3)
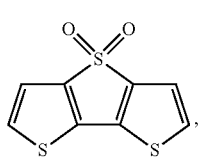
formula (ii-4)
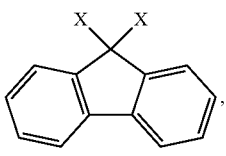
formula (ii-5)
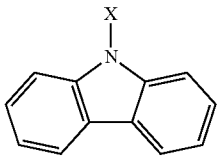
formula (ii-6)
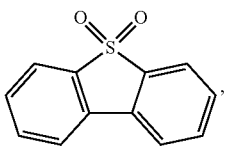
formula (ii-7)
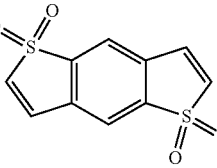
formula (ii-8)
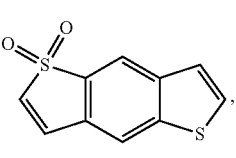
formula (ii-9)
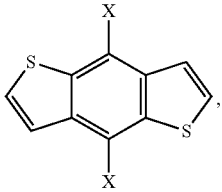
formula (ii-10)
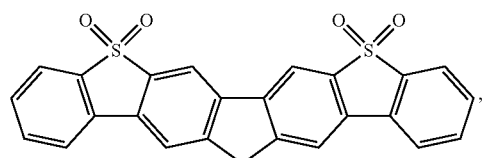
formula (ii-11)
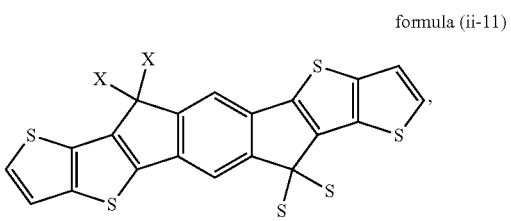
formula (ii-12)
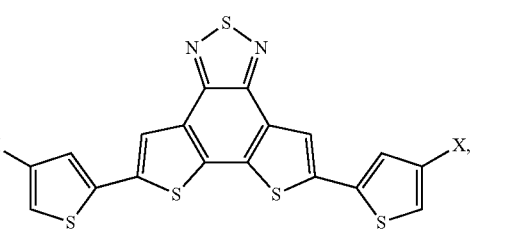
formula (ii-13)
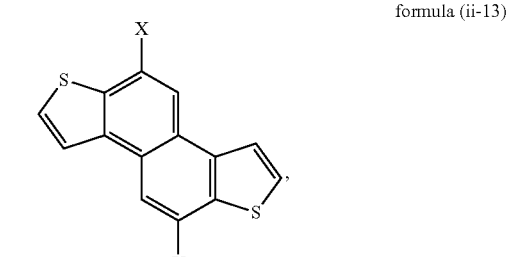
formula (ii-14)
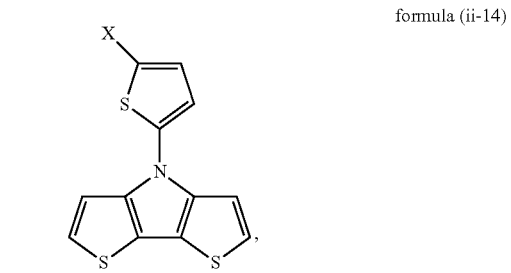
formula (ii-15)
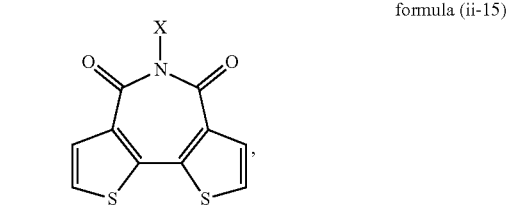

formula (ii-16)
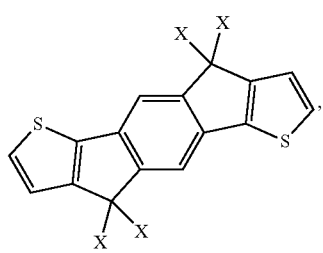
formula (ii-17)
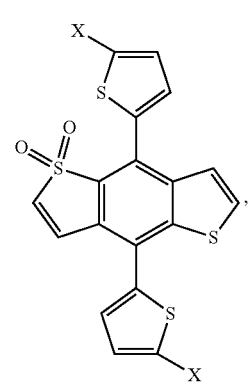
formula (ii-18)
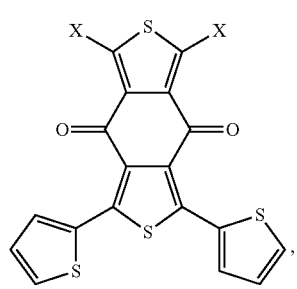
formula (ii-19)
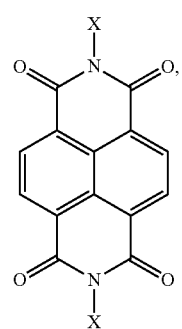
formula (ii-20)
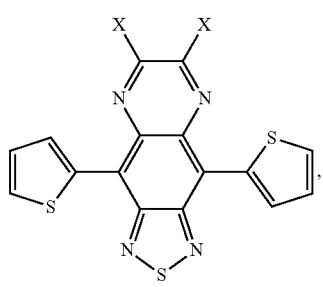
formula (ii-21)
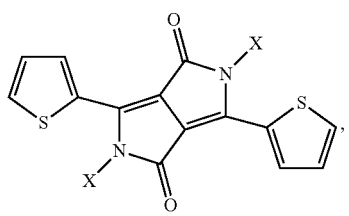
formula (ii-22)
formula (ii-23)
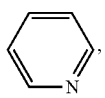
formula (ii-24)
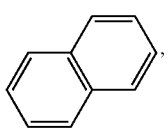
formula (ii-25)
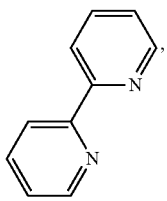
formula (ii-26)
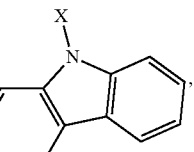
formula (ii-27)
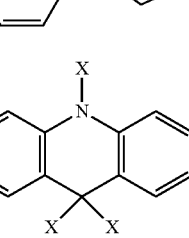
formula (ii-28)
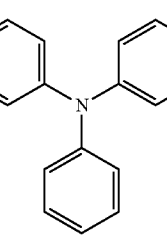
formula (ii-29)
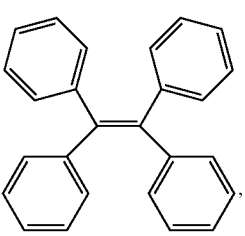

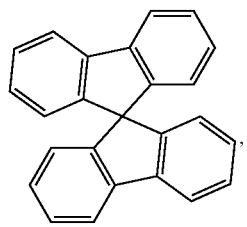
formula (ii-30)

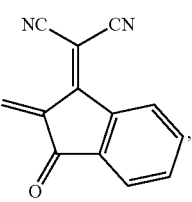
formula (ii-31)

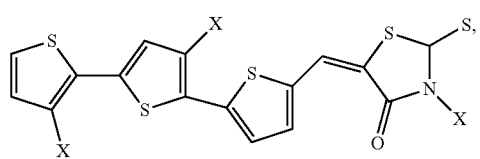
formula (ii-32)

wherein each X is independently an organic ring, which is substituted or unsubstituted, or an alkyl group with linear, branched or cyclic of 1 to 30 carbon atoms.

The aforementioned organic ring, which is substituted, means that at least one hydrogen atom on the organic ring can be substituted by the deuterium atom, the halogen atom or the monovalent group. The monovalent group can be but not limited to a hydroxyl group, a cyano group, a nitro group, an amino group, an amide group, a hydrazine group, a hydrazone group, an acetate or a salt thereof, a sulfonate or a salt thereof, a phosphate or a salt thereof, an alkyl group of 1 to 60 carbon atoms, an alkenyl group of 2 to 60 carbon atoms, an alkynyl group of 2 to 60 carbon atoms, an alkoxy group of 1 to 60 carbon atoms, a cycloalkyl group of 3 to 10 carbon atoms, a cycloalkenyl group of 3 to 10 carbon atoms, a heterocycloalkyl group of 3 to 10 carbon atoms, a heterocycloalkenyl group of 3 to 10 atoms, an aryl group of 6 to 30 carbon atoms, an aryloxy group of 6 to 30 carbon atoms, an arylthio group of 6 to 30 carbon atoms, a heteroaryl group of 2 to 30 carbon atoms, an aldehyde group or a silyl group. Furthermore, when at least two hydrogen atoms are substituted, the kinds of the substituted group can be the same or different. The common substituted group can be but not limited to the alkyl group of 1 to 60 carbon atoms, the aryl group of 6 to 30 carbon atoms or the heteroaryl group of 2 to 30 carbon atoms.

The organic ring can be but not limited to benzene, cyclopentadiene, indene, naphthalene, azulene, heptalene, indacene, acenaphthylene, fluorene, spiro-fluorene, phenalene, phenanthrene, anthracene, fluoranthene, triphenylene, pyrene, chrysene, thiophene, pyrrol, imidazole, pyrazole, triazole, thiazole, oxazole, isothiazole, isoxazole, benzothiazole, benzoimidazole, benzooxazole, pyridine, pyrazine, pyrimidine, pyridazine, isoindole, indole, indazole, purine, isoquinoline, quinoline, phthalazine, naphthyridine, quinoxaline, quinazoline, cinnoline, phenanthridine, acridine, phenanthroline or phenoxazine.

For example, the asymmetric fused aromatic ring derivative containing sulfonyl group of the present disclosure can include a structure represented by formula (I-1), formula (I-2), formula (I-3), formula (I-4), formula (I-5) or formula (I-6):

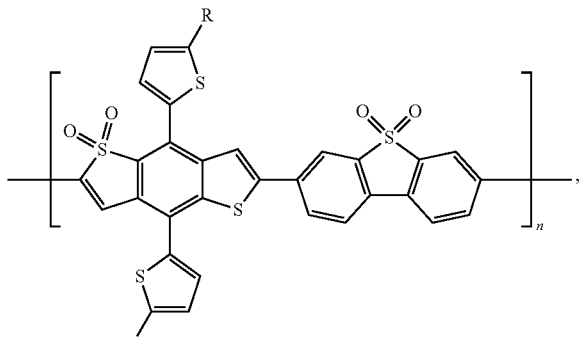
formula (I-1)

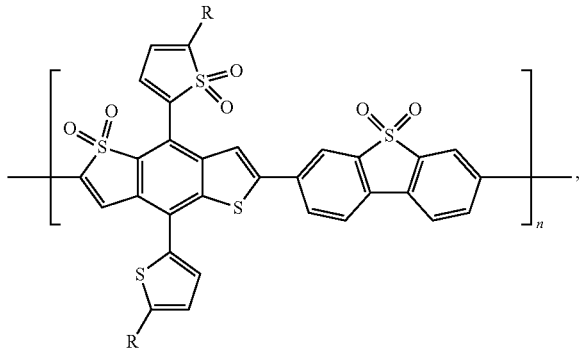
formula (I-2)

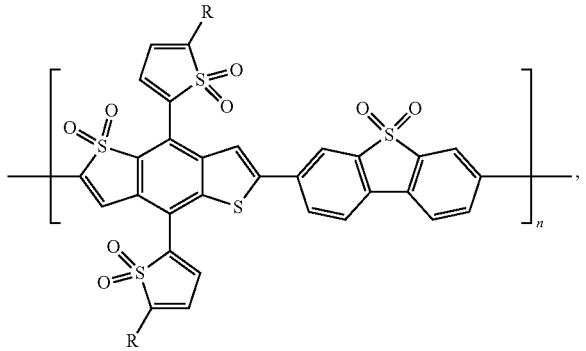
formula (I-3)

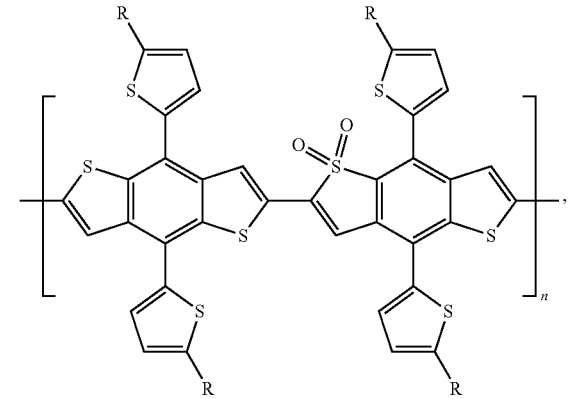
formula (I-4)

formula (I-5)

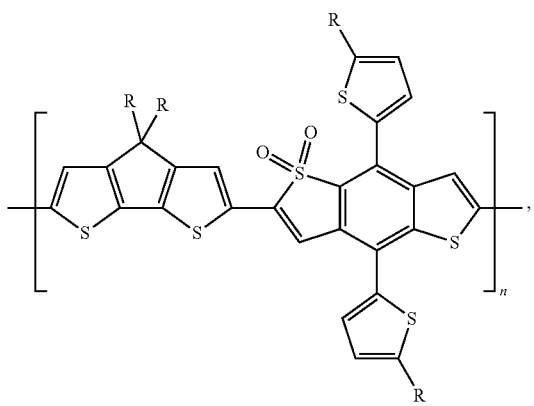

formula (I-6)

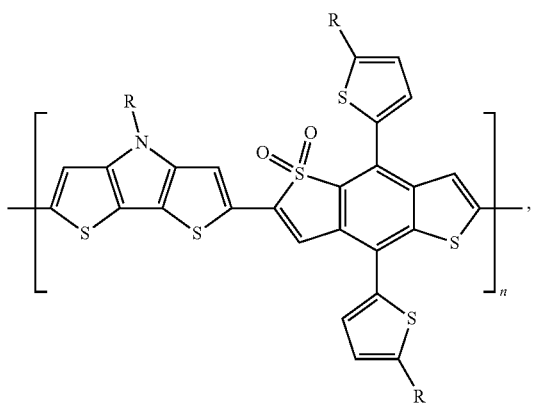

wherein R is 2-ethylhexyl, and n is an integer from 1 to 100.

The monomer unit in the asymmetric fused aromatic ring derivative containing sulfonyl group of the aforementioned formula (I-1), formula (I-2) and formula (I-3) is connected by Suzuki-Miyaura coupling method. Suzuki-Miyaura coupling method is an organic coupling reaction, which is the cross-coupling of the boronic acid or boronic ester of the aryl group or the alkenyl group with chlorine, bromine, iodo aromatic hydrocarbon or alkene under the metal catalysis.

The monomer unit in the asymmetric fused aromatic ring derivative containing sulfonyl group of the aforementioned formula (I-4) is connected by Stille coupling method. Stille coupling method is an organic coupling reaction, which is the cross-coupling of the organotin compound with chlorine, bromine, iodo aromatic hydrocarbon or alkene under the metal catalysis.

The monomer unit in the asymmetric fused aromatic ring derivative containing sulfonyl group of the aforementioned formula (I-5) and formula (I-6) is connected by direct arylation coupling method. Direct arylation coupling method is an organic coupling reaction, which is the cross-coupling of the organic molecules containing C—H bond with chlorine, bromine, iodo aromatic hydrocarbon or alkene under the metal catalysis.

A Use of the Asymmetric Fused Aromatic Ring Derivative Containing Sulfonyl Group A use of the asymmetric fused aromatic ring derivative containing sulfonyl group is provided of the present disclosure, the asymmetric fused aromatic ring derivative containing sulfonyl group can be used as a photocatalyst. When the asymmetric fused aromatic ring derivative containing sulfonyl group is applied to a hydrogen production device, the hydrogen evolution efficiency can be improved.

A Hydrogen Production Device

A hydrogen production device is provided of the present disclosure, the hydrogen production device includes a solution system. The solution system includes the aforementioned asymmetric fused aromatic ring derivative containing sulfonyl group and water, and the solution system can include an additive, such as a sacrificial agent. Specifically, when the light source illuminates the solution system, the hydrogen production device can be performed a photocatalytic hydrogen evolution from water splitting. Due to the asymmetric fused aromatic ring derivative containing sulfonyl group of the present disclosure has the photocatalytic activity, which is favorable for improving the efficiency of the hydrogen production device.

An Optoelectronic Component

An optoelectronic component is provided of the present disclosure, the optoelectronic component includes the aforementioned asymmetric fused aromatic ring derivative containing sulfonyl group, and the optoelectronic component can be but not limited to an organic solar cell, an organic light-emitting diode, an organic transistor, an organic photodetector or a biological imaging. The organic solar cell, the organic light-emitting diode, the organic transistor, the organic photodetector and the biological imaging are conventional technique, and will not be further described herein.

The present disclosure will be further exemplified by the following specific embodiments so as to facilitate utilizing and practicing the present disclosure completely by the people skilled in the art without over-interpreting and over-experimenting. However, the readers should understand that the present disclosure should not be limited to these practical details thereof, that is, these practical details are used to describe how to implement the materials and methods of the present disclosure and are not necessary.

Synthesis Example

The preparation of Synthesis Example 1 to Synthesis Example 3 of the present disclosure is that the reaction flask charged with 2,6-dibromo-4,8-bis(5-(2-ethylhexyl)thiophen-2-yl)benzo[1,2-b:4,5-b']dithiophene (BDTTBr), m-chloroperoxybenzoic acid (m-CPBA) and dichloromethane (DCM) are reacted at different temperatures. Next, the organic layer is acquired by washing with sodium bicarbonate ($NaHCO_3$), and extracted by water and DCM. Then, water in the organic layer is removed by anhydrous $MgSO_4$ and purified by using column chromatography. Finally, further purification is performed by adding ethanol until the precipitate is formed to obtain the product of Synthesis Example 1 to Synthesis Example 3. The content of the each component, the reaction temperature and the yield of Synthesis Example 1 to Synthesis Example 3 are shown in Table 1.

TABLE 1

|  | Synthesis Example 1 | Synthesis Example 2 | Synthesis Example 3 |
|---|---|---|---|
| BDTTBr (g) | 1.15 | 2.21 | 2.21 |
| m-CPBA (g) | 1.08 | 4.659 | 4.659 |
| DCM (mL) | 62.5 | 120 | 120 |
| reaction temperature (° C.) | 40 | 40 | 40 |
| yield (%) | 57.6 | 13.3 | 8.30 |

Synthesis Example 1 to Synthesis Example 3 of the present disclosure has a structure represented by formula (A), formula (B) and formula (C), respectively:

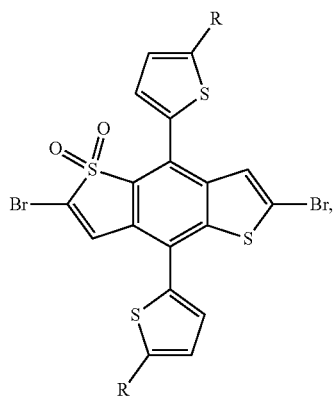

formula (A)

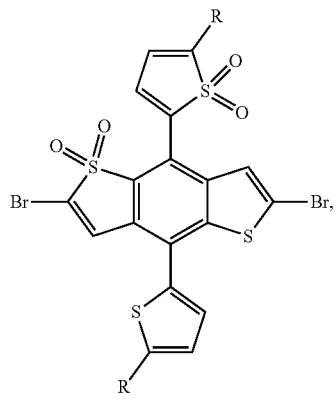

formula (B)

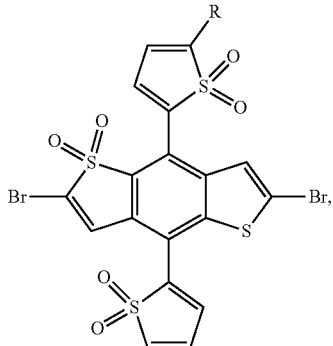

formula (C)

wherein R is 2-ethylhexyl.

Example/Comparative Example

The preparation of Example 1 to Example 3 of the present disclosure is that a monomer of Synthesis Example, sodium carbonate ($Na_2CO_3$), tetrakis(triphenylphosphine)palladium ($Pd(PPh_3)_4$), tetrabutylammonium bromide (TBAB), water, toluene and 3,7-bis(4,4,5,5-tetramethyl-1,3,2-dioxaborolan-2-yl)dibenzo[b,d]thiophene5,5-dioxide (BSO) monomer are mixed to a mixture. Next, the mixture is evacuated and degassed by nitrogen for 30 minutes, and then refluxed for 72 hours. Furthermore, the mixture is poured into methanol, and washed with methanol, hexane, chloroform and water to remove reactants and by-products. Finally, the polymer is collected and dried under vacuum to obtain the asymmetric fused aromatic ring derivative containing sulfonyl group of Example 1 to Example 3. The content of the each component and Synthesis Example type of Example 1 to Example 3 are shown in Table 2.

TABLE 2

| Synthesis Example | Example 1 Synthesis Example 1 | Example 2 Synthesis Example 2 | Example 3 Synthesis Example 3 |
|---|---|---|---|
| content | | | |
| Synthesis Example (mg) | 692 | 320 | 208 |
| BSO (mg) | 421 | 187 | 117 |
| $Na_2CO_3$ (mg) | 2289 | 1017 | 636 |
| $Pd(PPh_3)_4$ (mg) | 50 | 22 | 16 |
| TBAB (mg) | 11.7 | 5.2 | 3.2 |
| water (mL) | 9 | 4 | 2.5 |
| toluene (mL) | 35 | 15 | 10 |

Furthermore, the preparation of Comparative Example 1 of the present disclosure is that 736 mg of BDTTBr monomer, 2544 mg of sodium carbonate, 55 mg of tetrakis (triphenylphosphine)palladium, 13 mg of tetrabutylammonium bromide, 10 mL of water, 40 mL of toluene and 468 mg of BSO monomer are mixed to a mixture, and other steps are the same as those of Example 1 to Example 3 to obtain the product of Comparative Example 1.

Example 1 to Example 3 and Comparative Example 1 of the present disclosure are performed the coupling by Suzuki-Miyaura coupling method. Taking Example 1 as an example, the reaction of Example 1 is shown in Table 3.

TABLE 3

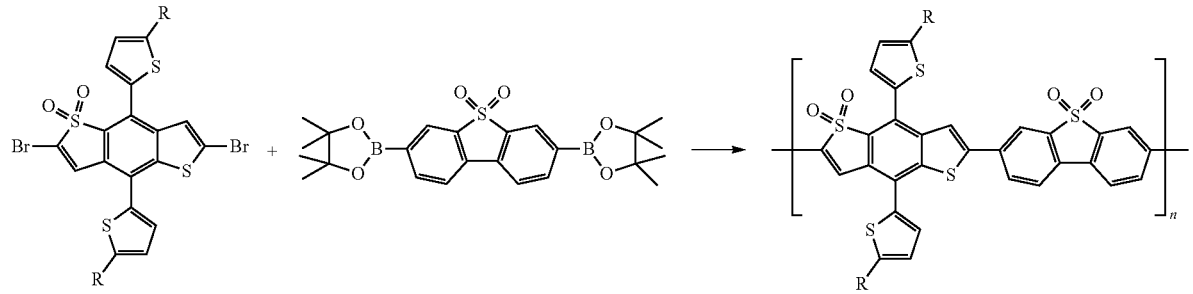

The preparation of Example 4 of the present disclosure is that 0.215 g of Synthesis Example 1, 0.253 g of 4,8-bis(5-(2-ethylhexyl)thiophen-2-yl)benzo[1,2-b:4,5-b']dithiophene-2,6-diyl-bis(trimethylstannane) monomer, 0.004 g of tris(dibenzylideneacetone)dipalladium, 0.014 g of tri(2-methylphenyl)phosphine and 25 mL of anhydrous dimethylformamide (DMF) are mixed to a mixture in the round-bottom flask. Next, the mixture is vented by nitrogen for 20 minutes, and reacted at 150° C. for 48 hours. After the reaction, the mixture is washed with methanol and hexane to remove reactants and by products. Finally, the polymer is eluted with high temperature chloroform and poured into methanol to precipitate to obtain the asymmetric fused aromatic ring derivative containing sulfonyl group of Example 4.

Example 4 of the present disclosure is performed the coupling by Stille coupling method, the reaction of Example 4 is shown in Table 4.

TABLE 4

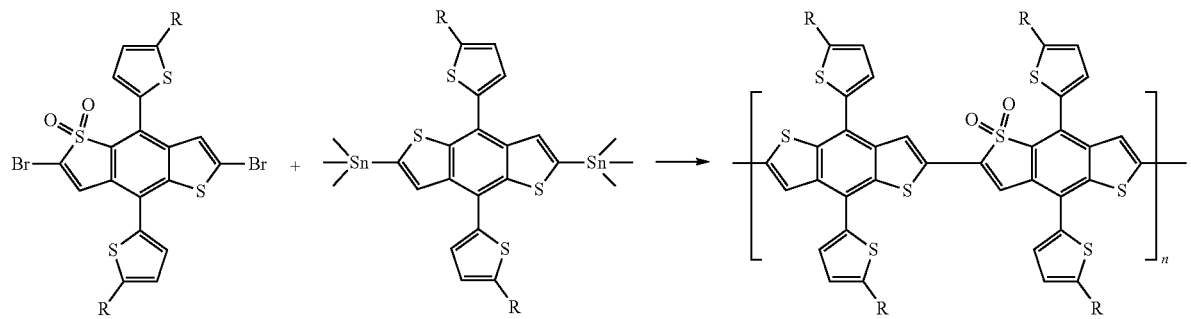

The preparation of Example 5 of the present disclosure is that 0.54 g of Synthesis Example 1, 0.28 g of 4,4-bis(2-ethylhexyl)-4H-cyclopenta[2,1-b:3,4-b']dithiophene monomer, 0.24 g of potassium carbonate, 0.021 g of trimethylacetic acid, 0.0157 g of palladium (II) acetate and 7.056 mL of dimethylformamide are mixed to a mixture in the round-bottom flask. Next, the mixture is vented by nitrogen for 20 minutes, and reacted at 80° C. for 20 hours. The remaining steps are the same as those of Example 4 to obtain the asymmetric fused aromatic ring derivative containing sulfonyl group of Example 5.

Example 5 of the present disclosure is performed the coupling by Direct arylation coupling method, the reaction of Example 5 is shown in Table 5.

TABLE 5

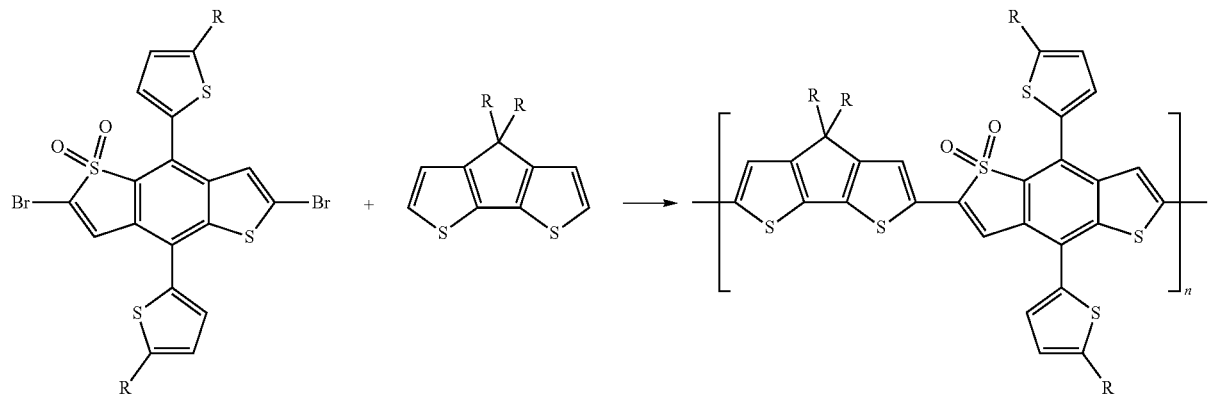

The preparation of Example 6 of the present disclosure is that 0.85 g of Synthesis Example 1, 0.326 g of 4-(2-ethylhexyl)-4H-dithieno[3,2-b:2',3'-d]pyrrole monomer, 0.38 g of potassium carbonate, 0.034 g of trimethylacetic acid, 0.025 g of palladium (II) acetate and 11.088 mL of dimethylformamide are mixed to a mixture in the round-bottom flask. Next, the mixture is vented by nitrogen for 20 minutes, and reacted at 80° C. for 20 hours. The remaining steps are the same as those of Example 4 to obtain the asymmetric fused aromatic ring derivative containing sulfonyl group of Example 6.

Example 6 of the present disclosure is performed the coupling by Direct arylation coupling method, the reaction of Example 6 is shown in Table 6.

TABLE 6

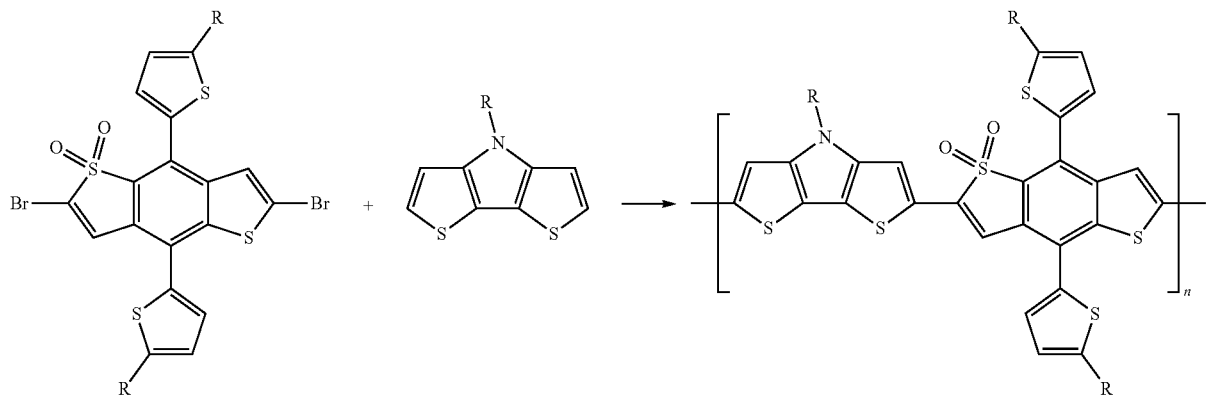

Specifically, Example 1 to Example 6 and Comparative Example 1 of the present disclosure has a structure represented by formula (I-1), formula (I-2), formula (I-3), formula (I-4), formula (I-5), formula (I-6), and formula (I-7), respectively:
formula (I-1)
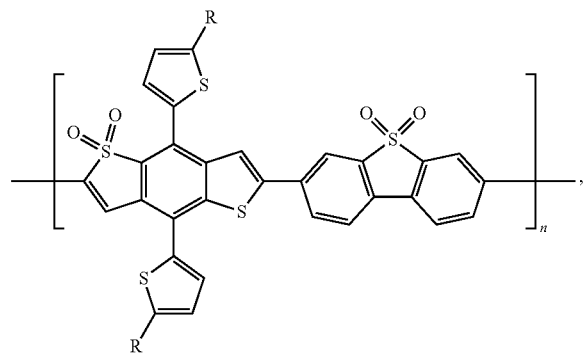
formula (I-2)
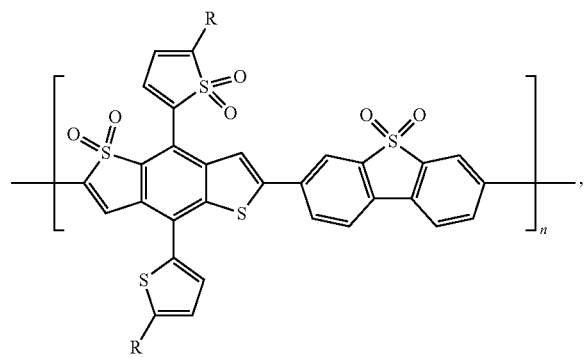
formula (I-3)
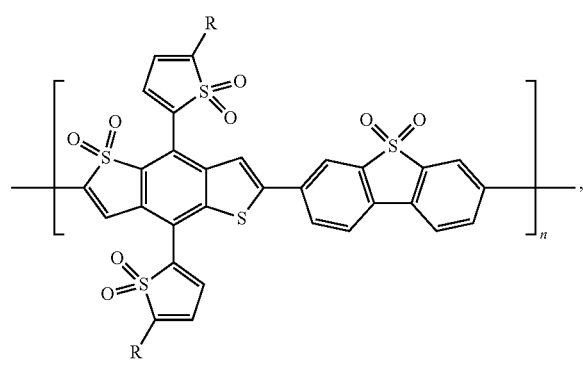
formula (I-4)
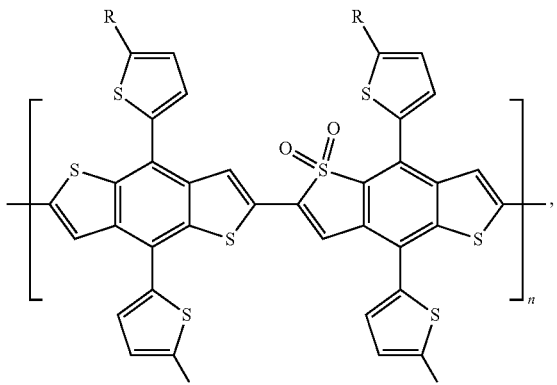
formula (I-5)
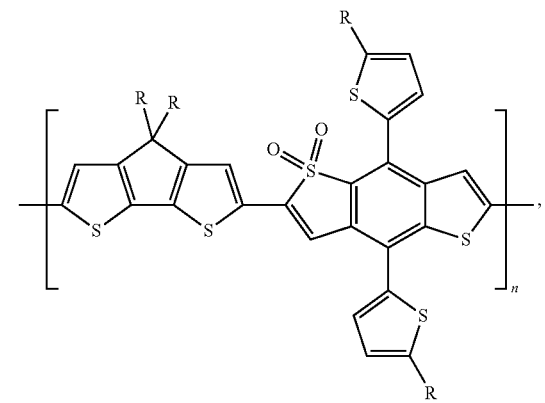
formula (I-6)
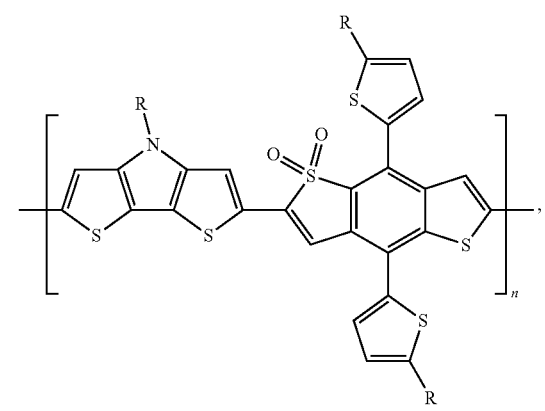

-continued formula (I-7)

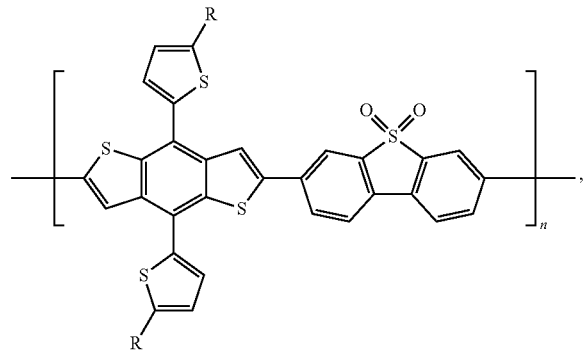

wherein R is 2-ethylhexyl.

The Physical Property Test of Example/Comparative Example

Please refer to FIG. 1, which is a $^{13}C$ NMR spectrum of Example 1 to Example 3 and Comparative Example 1 to determine the structure of the asymmetric fused aromatic ring derivative containing sulfonyl group. As shown in FIG. 1, it can be seen that the characteristic peaks between 10 ppm to 50 ppm are mainly alkyl side chains, and the characteristic peaks between 120 ppm to 160 ppm are mainly aromatic carbon. Specifically, the characteristic peaks located at 42 ppm and 37 ppm can be assigned to the carbon atom adjacent to the thiophene and thiophene 1, 1-dioxide in the side chain, respectively. Hence, the peak intensity at 42 ppm gradually decreased as thiophene is oxidized to thiophene 1, 1-dioxide in the side chain.

Figure 2:
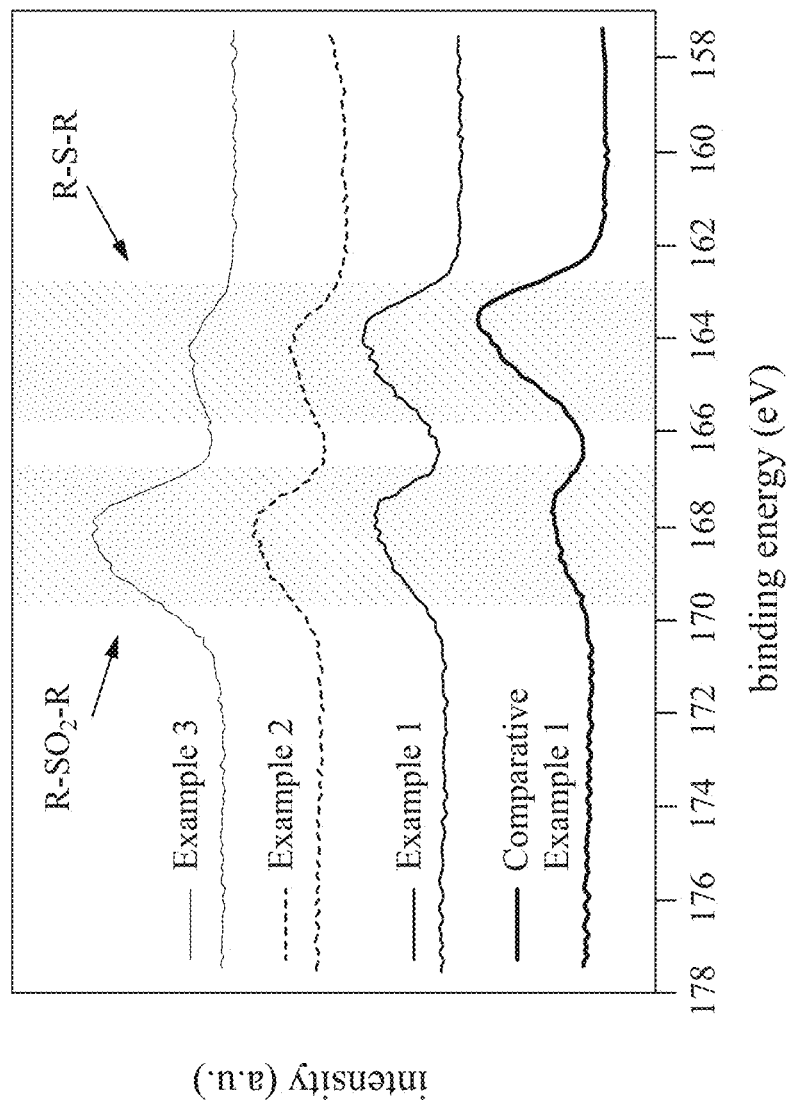
FIG. 2 is a XPS diagram of Example 1 to Example 3 and Comparative Example 1.

Please refer to FIG. 2, which is a XPS diagram of Example 1 to Example 3 and Comparative Example 1 to characterize the different chemical bonding state of sulfur. As shown in FIG. 2, it can be seen that the characteristic peaks located between 162 eV and 166 eV are R—S—R, and the characteristic peaks located between 167 eV and 170 eV are R—$SO_2$—R. Furthermore, the theoretical ratio of R—$SO_2$—R and R—S—R of Example 1 to Example 3 and Comparative Example 1 are 2:3, 3:2, 4:1 and 1:4, which is consistent with the results of FIG. 2.

Figure 3:
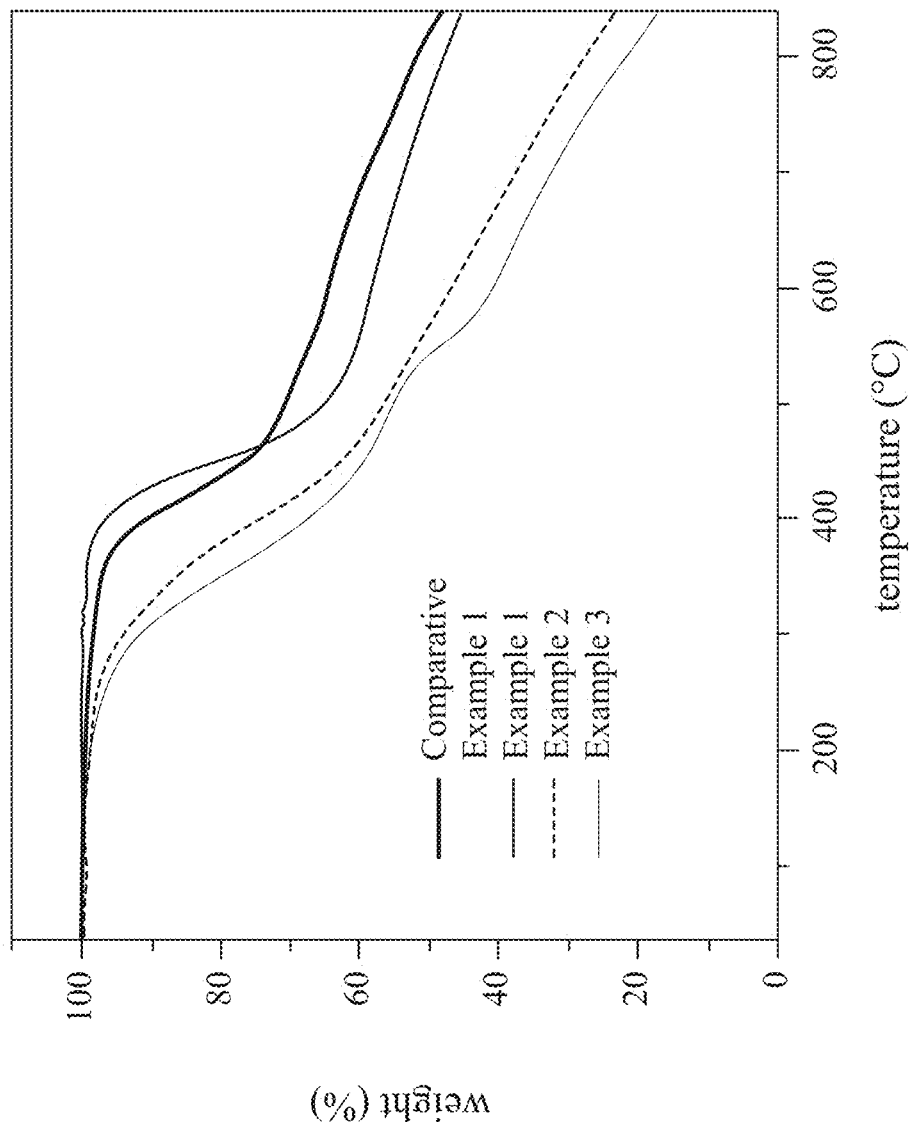
FIG. 3 is a TGA diagram of Example 1 to Example 3 and Comparative Example 1.

Please refer to FIG. 3, which is a TGA diagram of Example 1 to Example 3 and Comparative Example 1. The thermogravimetric analysis is performed by using the thermogravimetric analyzer (model is TA Q600) to obtain the decomposition temperature (Td) under the conditions of the temperature range of 30° C. to 800° C. and $N_2$ atmosphere, so as to confirm the thermal stability of the asymmetric fused aromatic ring derivative containing sulfonyl group, and the results are recorded in Table 7. The results showed that Example 1 has the thermal stability under the $N_2$ atmosphere, and Example 2 and Example 3 has the lower thermal stability due to the poor solubility and large steric hindrance of the monomer in the polymerization.

TABLE 7

| | Example 1 | Example 2 | Example 3 | Comparative Example 1 |
|---|---|---|---|---|
| $T_d$ (° C.) | 409.2 | 292.3 | 273.2 | 373.4 |

The Photophysical Property Test of Example/Comparative Example

Figure 4:
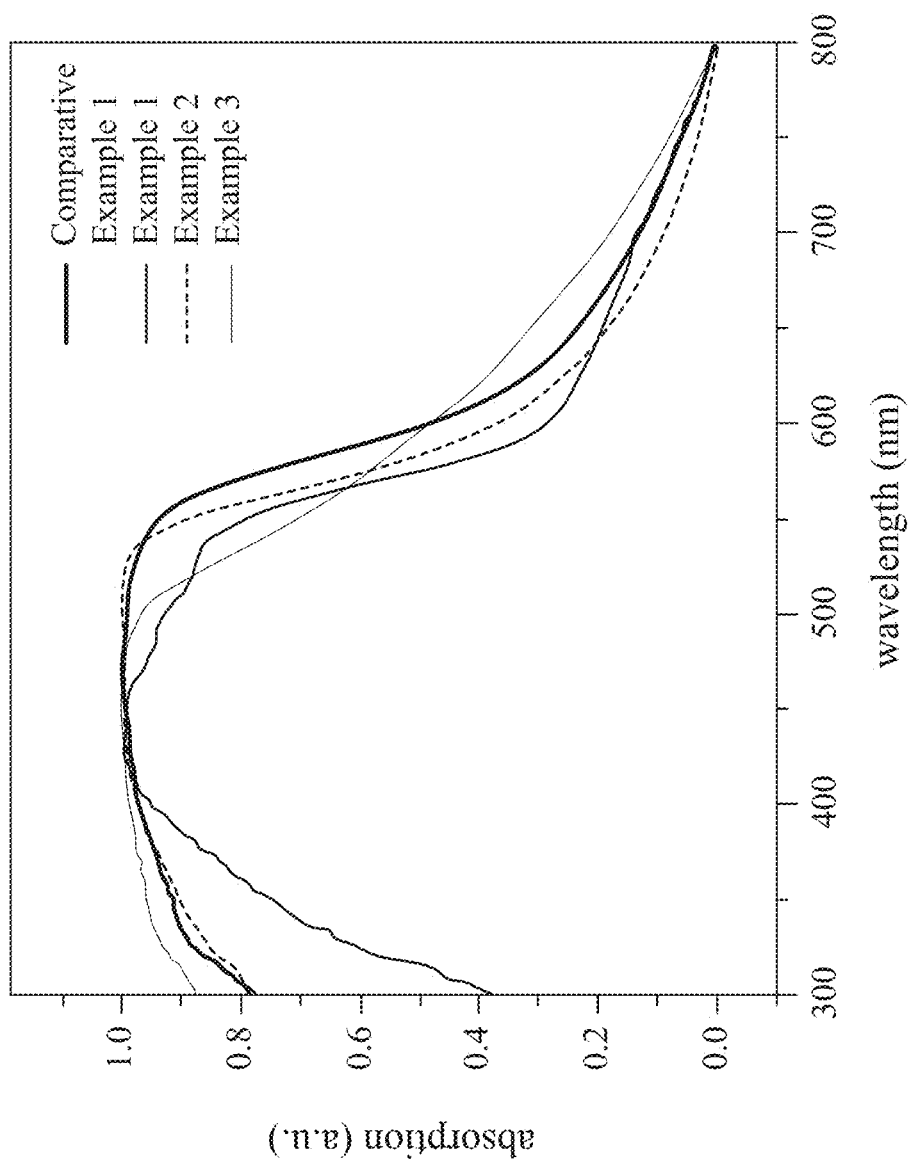
FIG. 4 is an UV-Vis DRS diagram of Example 1 to Example 3 and Comparative Example 1.

Please refer to FIG. 4, which is an UV-Vis DRS diagram of Example 1 to Example 3 and Comparative Example 1. The ultraviolet-visible diffuse reflectance spectroscopy analysis is measured by using spectrophotometer (model is Hitachi U-3300) to confirm the light absorption property of the asymmetric fused aromatic ring derivative containing sulfonyl group. The optical bandgap (Eg) can be calculated by the Tauc-Plot, and the results are recorded in Table 8.

Figure 5:
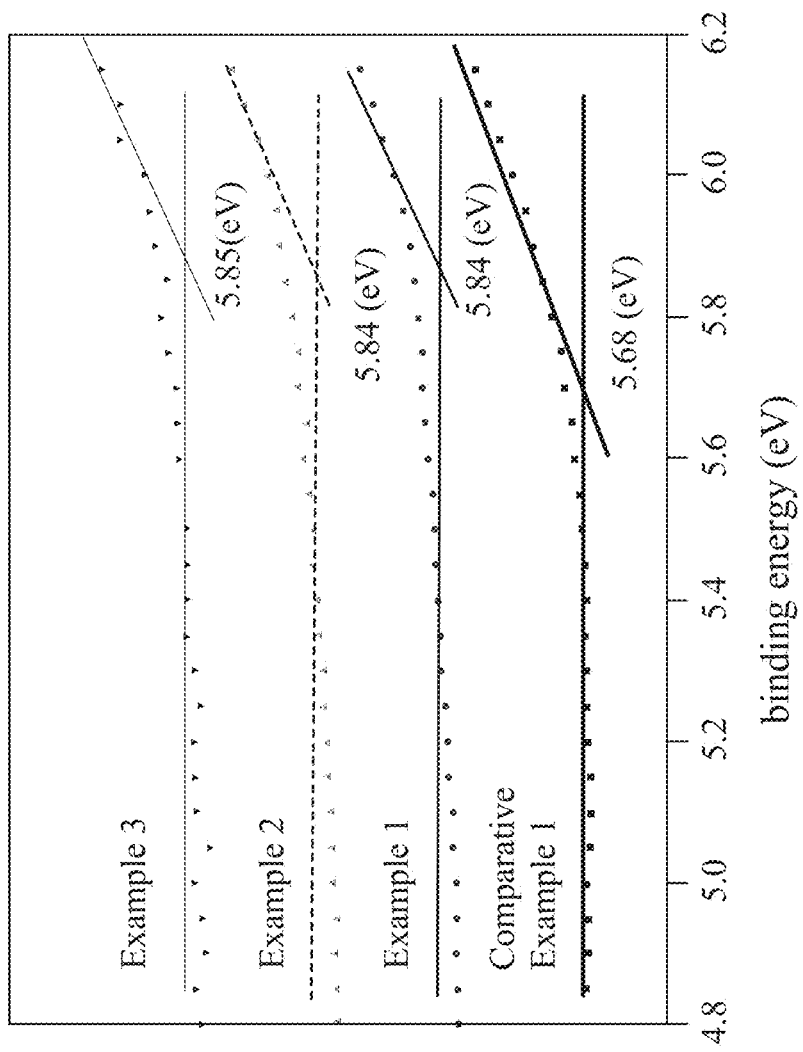
FIG. 5 is a photoelectron spectroscopy of Example 1 to Example 3 and Comparative Example 1.

Please refer to FIG. 5, which is a photoelectron spectroscopy of Example 1 to Example 3 and Comparative Example 1. The HOMO energy level is measured by photoelectron spectrometer (model is AC-II), and the LUMO energy level is the difference obtained by subtracting the optical energy gap ($E_g$) from the HOMO energy level, and the results are recorded in Table 8.

TABLE 8

| | $E_g$ (eV) | HOMO (eV) | LUMO (eV) |
|---|---|---|---|
| Example 1 | 2.12 | −5.84 | −3.72 |
| Example 2 | 2.13 | −5.84 | −3.71 |
| Example 3 | 2.17 | −5.85 | −3.68 |
| Comparative Example 1 | 2.04 | −5.68 | −3.64 |

As shown in Table 8, due to the intramolecular charge transfer and the introduction of electron-withdrawing functional group, the HOMO energy level and the LUMO energy level of Example 1 to Example 3 are lower than those of Comparative Example 1.

The Photocatalytic Property Test of Example/Comparative Example

Figure 6:
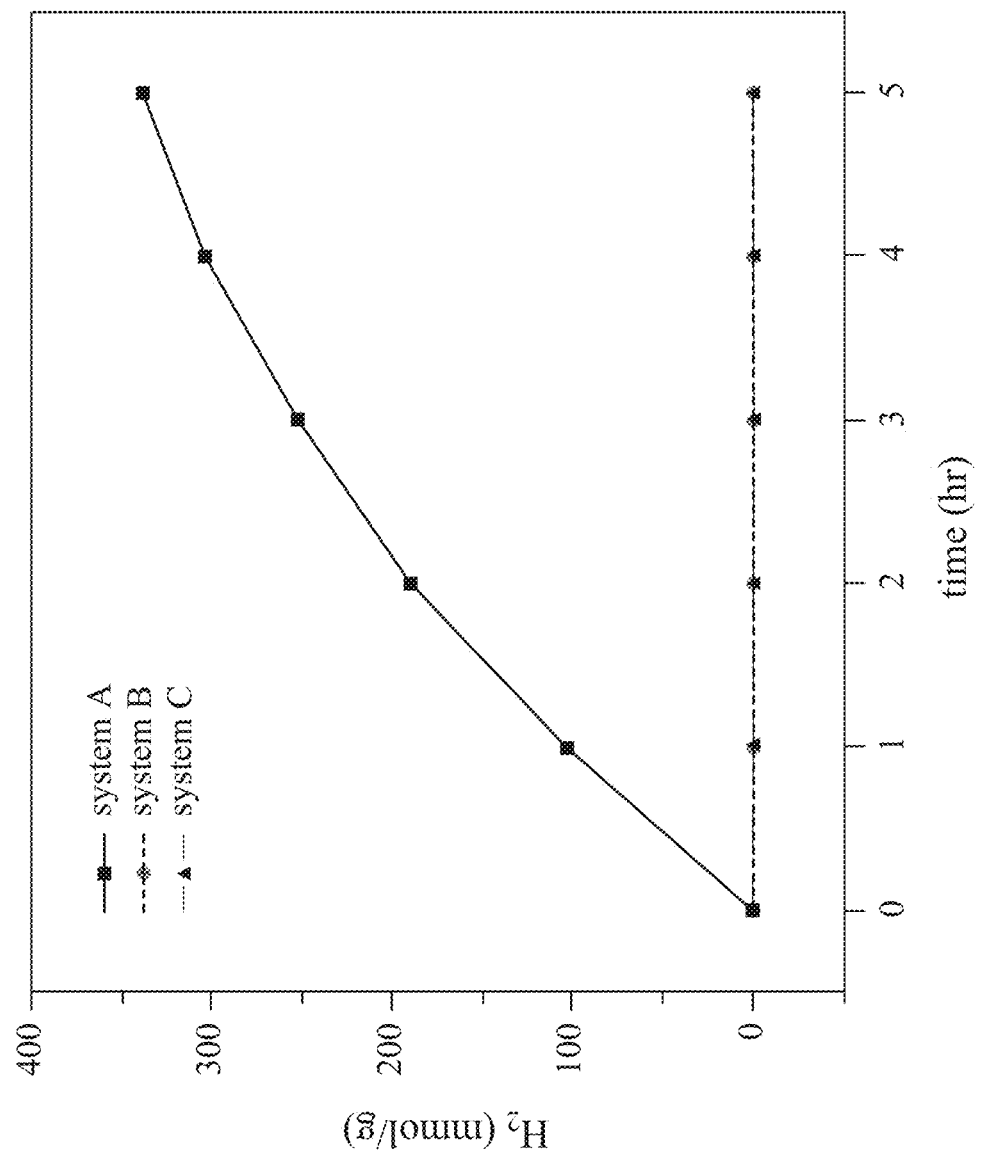
FIG. 6 is a result diagram of the photocatalytic hydrogen evolution from water splitting of system A, system B and system C.

Observing the effect of the photocatalytic hydrogen evolution from water splitting as following three systems. System A is to add the asymmetric fused aromatic ring derivative containing sulfonyl group of Example 1 to water. System B has only water, and System C has only the asymmetric fused aromatic ring derivative containing sulfonyl group of Example 1. The photocatalytic hydrogen evolution from water splitting of the abovementioned systems are all performed under the illumination condition. Please refer to FIG. 6, which is a result diagram of the photocatalytic hydrogen evolution from water splitting of system A, system B and system C. As shown in FIG. 6, the hydrogen production of system B and system C is 0, that is, only water or only the asymmetric fused aromatic ring derivative containing sulfonyl group of Example 1 cannot provide the catalytic activity of hydrogen evolution from water splitting. In contrast, system A contains both water and the asymmetric fused aromatic ring derivative containing sulfonyl group of Example 1, and under the irradiation of the light source, the hydrogen production of system A rises. That is, the asymmetric fused aromatic ring derivative containing sulfonyl group of Example 1 can be used as the photocatalyst, which is indispensable with water.

Furthermore, Example 1 to Example 3 and Comparative Example 1 are performed the photocatalytic hydrogen evolution from water splitting experiment. First, 2 mg of Example 1 to Example 3 and Comparative Example 1 are respectively added into the reactor with 1 mL of NMP solvent to perform sonication for 10 minutes. Next, 9 mL of water, 3 wt % of co-catalyst $H_2PtCl_6$ and the sacrificial agent are added, and potassium hydroxide is used to adjust different pH value to form the solution system, wherein the sacrificial agent can be ascorbic acid (AA), triethylamine (TEA) or triethanolamine (TEOA). The Example/Comparative Example, the type and the concentration of the sacrificial agent of each solution systems, and the pH value of solution system are listed in Table 9.

TABLE 9

| Example/<br>Comparative Example | | sacrificial<br>agent | pH value |
|---|---|---|---|
| Example 7 | Example 1 | 1M AA | 4.0 |
| Example 8 | Example 2 | 1M AA | 4.0 |
| Example 9 | Example 3 | 1M AA | 4.0 |
| Comparative Example 2 | Comparative Example 1 | 1M AA | 4.0 |
| Comparative Example 3 | Example 1 | 1M TEA | 4.0 |
| Comparative Example 4 | Example 1 | 1M TEOA | 4.0 |
| Comparative Example 5 | Example 1 | 1M AA | 1.89 |
| Comparative Example 6 | Example 1 | 0.1M AA | 4.0 |

Afterward, the solution systems of Example 7 to Example 9 and Comparative Example 2 to Comparative Example 6 are degassed by argon, kept under the negative pressure, and illuminated by the 350 W Xe lamp as the light source. The relationship between the hydrogen production and time is measured by gas chromatography (GC) to obtain the hydrogen evolution rate (HER), and the results are recorded in Table 10.

Figure 7:
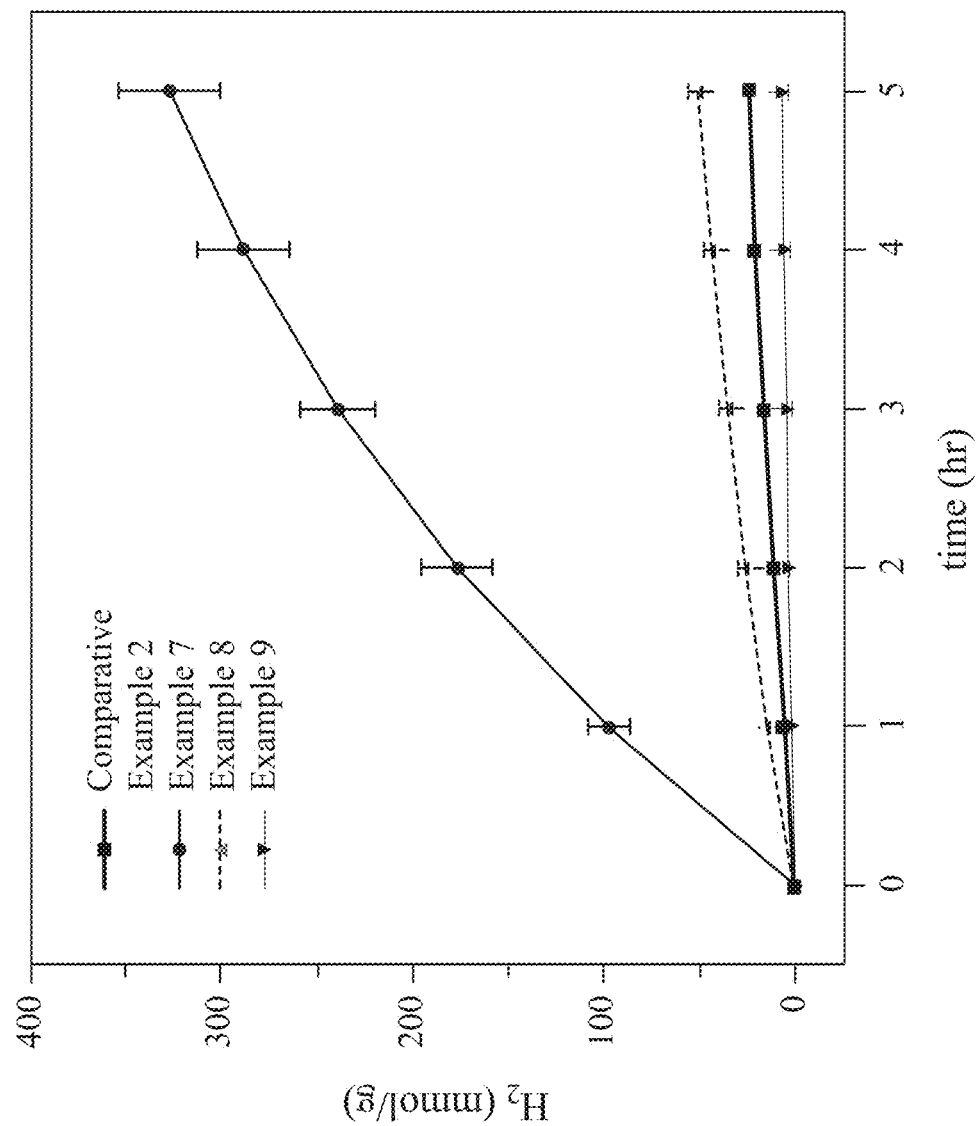
FIG. 7 is a result diagram of the photocatalytic hydrogen evolution from water splitting of Example 7 to Example 9 and Comparative Example 2.
Figure 8:
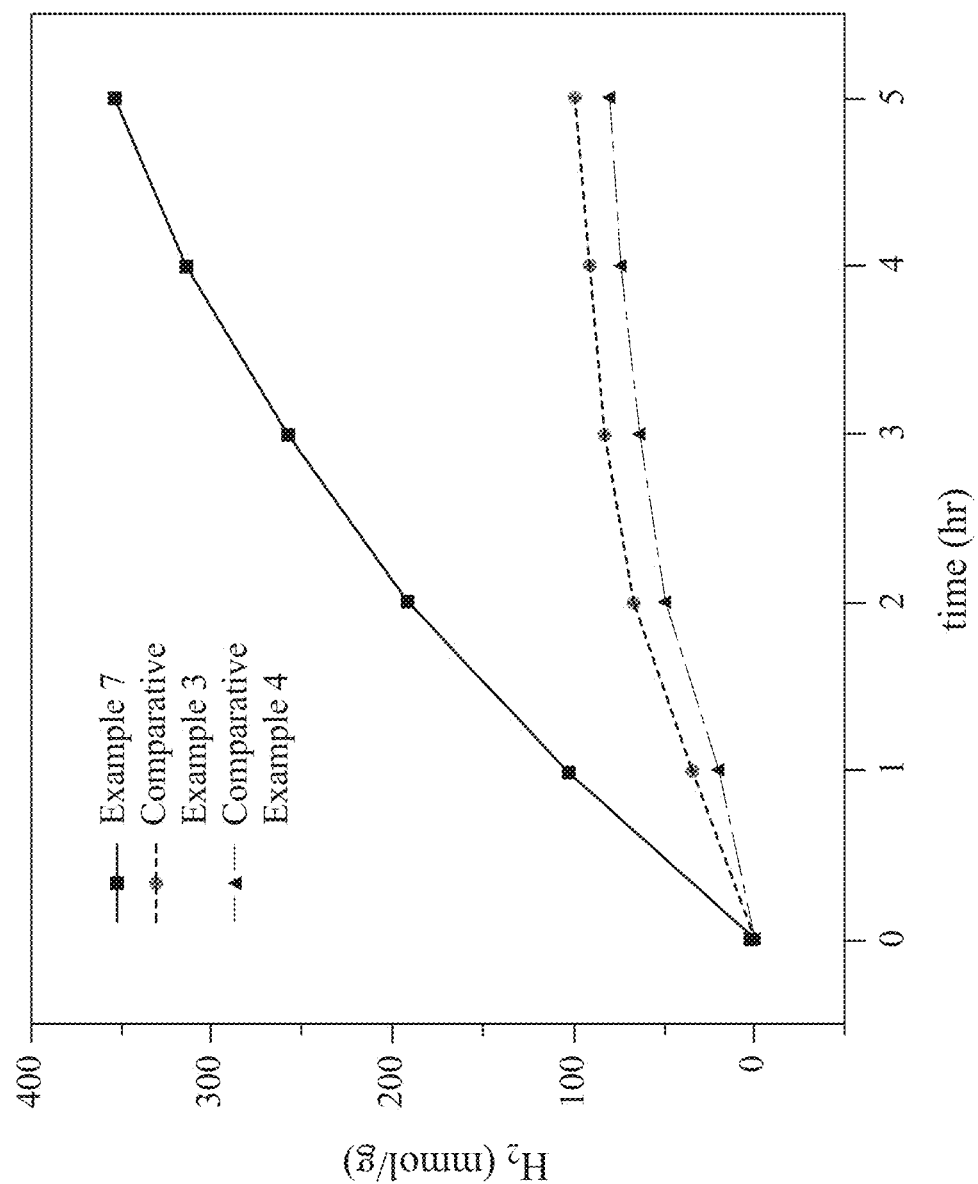
FIG. 8 is a result diagram of the photocatalytic hydrogen evolution from water splitting of Example 7, Comparative Example 3 and Comparative Example 4.
Figure 9:
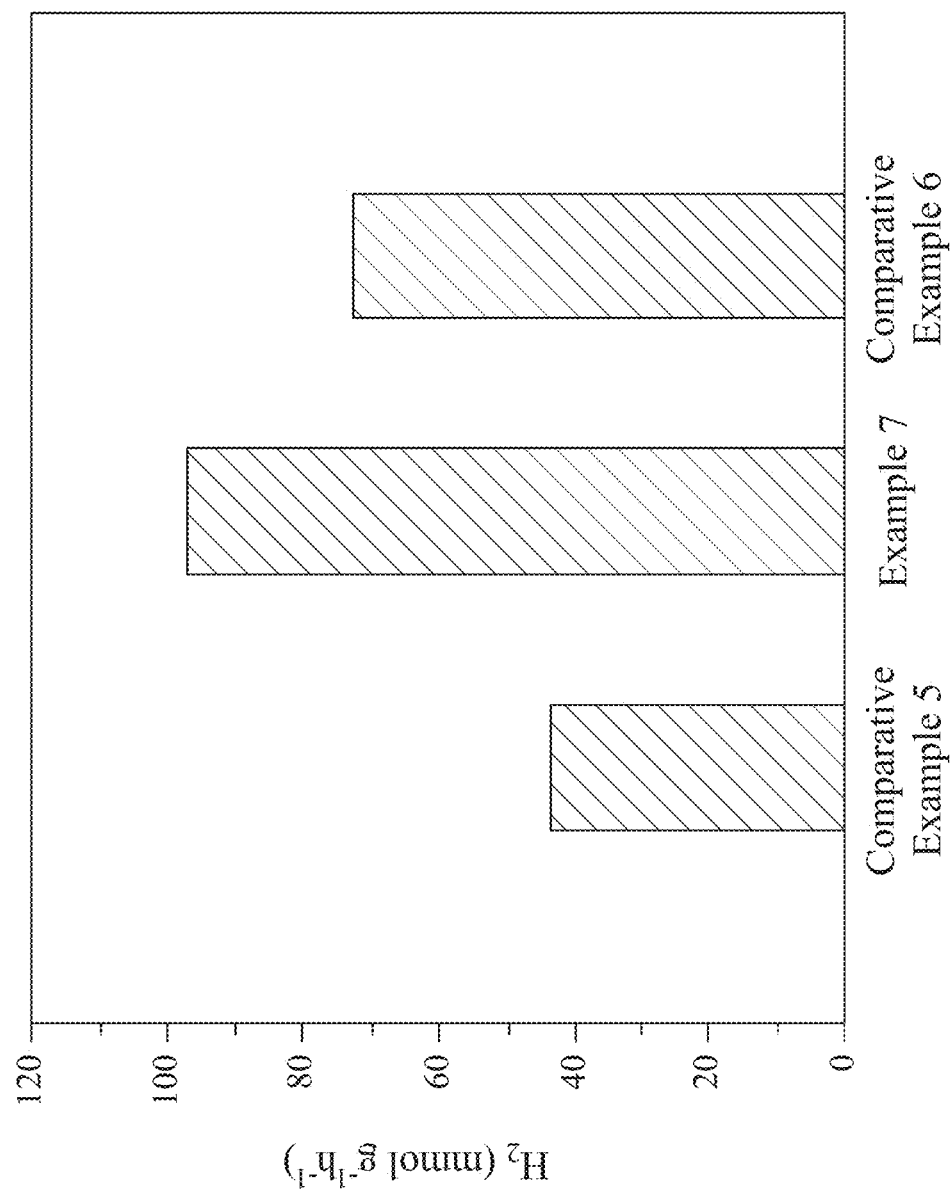
FIG. 9 is a histogram of the photocatalytic hydrogen evolution from water splitting of Example 7, Comparative Example 5 and Comparative Example 6.

Please refer to FIG. 7, FIG. 8 and FIG. 9, wherein FIG. 7 is a result diagram of the photocatalytic hydrogen evolution from water splitting of Example 7 to Example 9 and Comparative Example 2. FIG. 8 is a result diagram of the photocatalytic hydrogen evolution from water splitting of Example 7, Comparative Example 3 and Comparative Example 4. FIG. 9 is a histogram of the photocatalytic hydrogen evolution from water splitting of Example 7, Comparative Example 5 and Comparative Example 6. As shown in FIG. 7, it can be seen that with the increase of the content of the sulfonyl group, the HER shows a downward trend. However, Example 7 has better hydrogen evolution rate than that of Comparative Example 2, indicating that the asymmetric fused aromatic ring derivative containing sulfonyl group of Example 1 has better effect of the photocatalytic hydrogen evolution from water splitting than that of Comparative Example 1. It can be proved that A1-A2 type of conjugated polymer has the great potential for photocatalyst. Furthermore, as shown in FIG. 8 and FIG. 9, different types and concentrations of the sacrificial agent and the pH value of the solution system will affect the photocatalytic hydrogen evolution from water splitting efficiency. Preferably, the sacrificial agent is AA, and the pH value of the solution system is preferably 4.0.

TABLE 10

| | HER (mmol h$^{-1}$ g$^{-1}$) |
|---|---|
| Example 7 | 97.1 |
| Example 8 | 15.1 |
| Example 9 | 1.73 |
| Comparative Example 2 | 5.85 |
| Comparative Example 3 | 32.9 |
| Comparative Example 4 | 28.9 |
| Comparative Example 5 | 43.6 |
| Comparative Example 6 | 72.6 |

Figure 10:
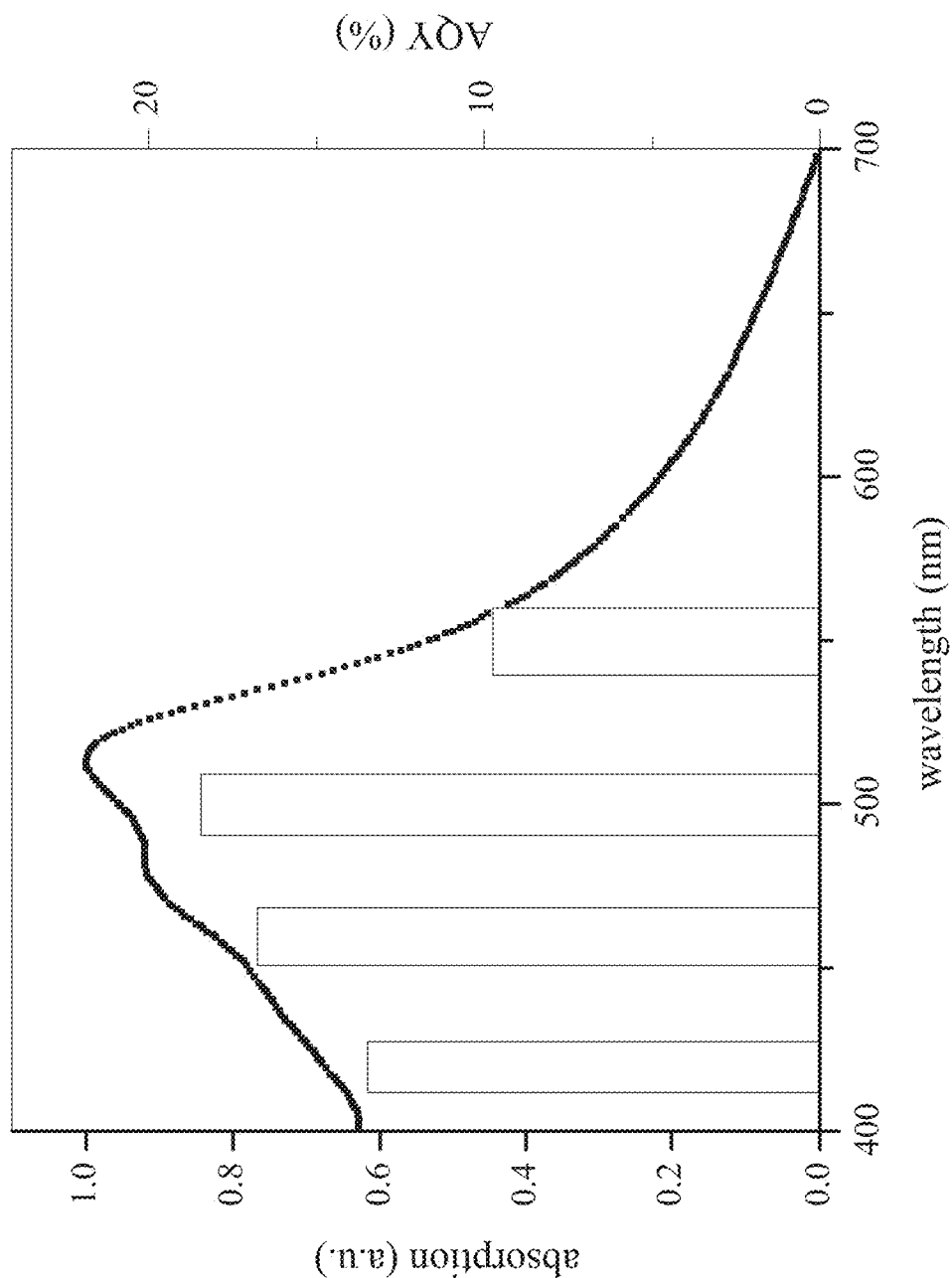
FIG. 10 is a result diagram of the apparent quantum yield of Example 7 with different wavelength.

Please refer to FIG. 10, which is a result diagram of the apparent quantum yield of Example 7 with different wavelength. Specifically, the apparent quantum yield (AQY) is defined as the ratio of the number of reacted electrons to the number of incident photons under a specific wavelength. Example 7 is irradiated with monochromatic light of 420 nm, 460 nm, 500 nm and 550 nm, and the irradiation area and the irradiation time are 6 cm$^2$ and 3600 s, respectively, so as to measure the light intensity of each wavelength and the amount of hydrogen gas at each wavelength of Example 7, and substitute they into the formula to obtain the AQY. The results are listed in Table 11, wherein the relevant formula of the AQY is well known in the art, and will not be described herein. Currently, most of polymer photocatalysts show the high AQY at wavelengths between 400 nm to 500 nm, but the AQY is dramatically decreased at wavelength larger than 500 nm. However, the maximum radiation intensity of the solar spectrum occurs at 500 nm to 600 nm, so the AQY in the above wavelength range is very important. As shown in FIG. 10, it can be seen that Example 7 still has the excellent AQY at 500 nm and 550 nm, so that the AQY of the asymmetric fused aromatic ring derivative containing sulfonyl group of the present disclosure breaks the record in the current related field.

TABLE 11

| wavelength (nm) | light intensity (W/m$^2$) | amount of hydrogen gas (μmol) | AQY (%) |
|---|---|---|---|
| 420 | 80 | 40.95 | 13.5 |
| 460 | 60 | 41.76 | 16.7 |
| 500 | 70 | 58.43 | 18.5 |
| 550 | 70 | 33.94 | 9.80 |

The Particle Aggregation Test of Example/Comparative Example

Figure 11:
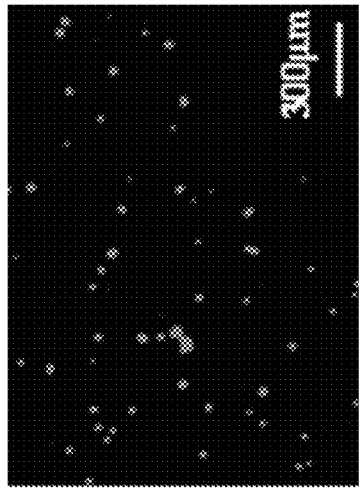
FIG. 11 is a fluorescence microscopy image of Example 1 to Example 3 and Comparative Example 1.
Figure 11:
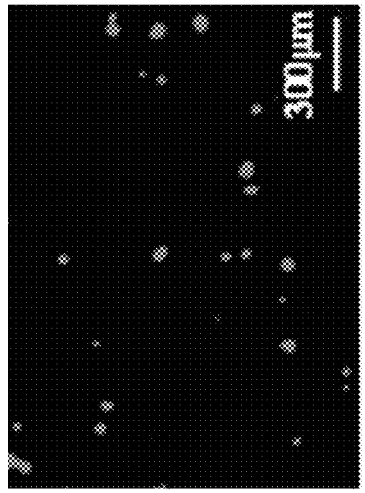
Figure 11:
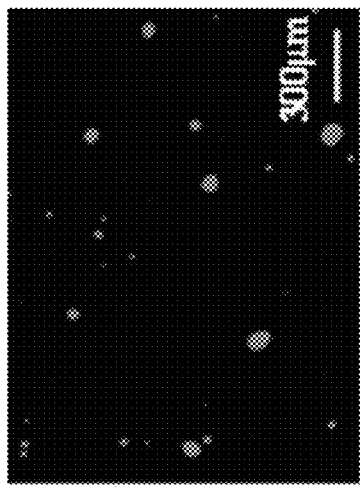
Figure 12:
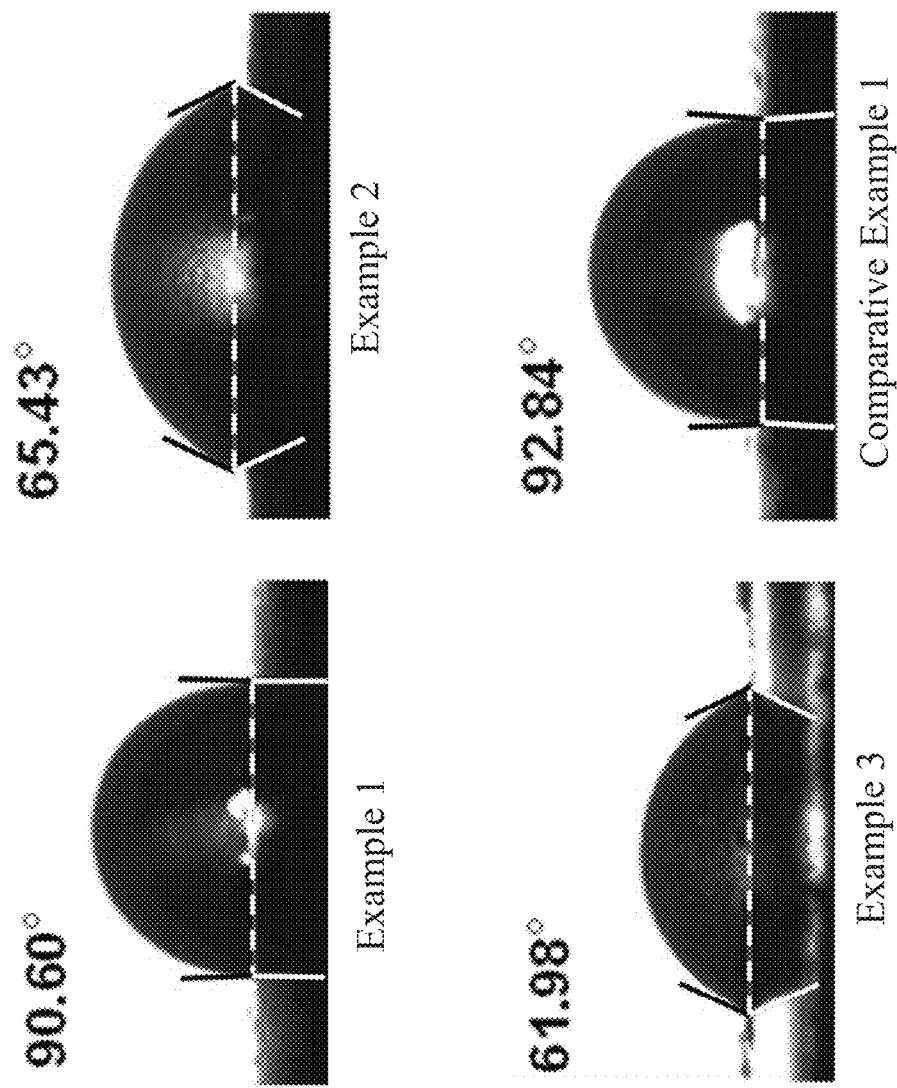
FIG. 12 is a contact angle image of Example 1 to Example 3 and Comparative Example 1 with water.
Figure 13:
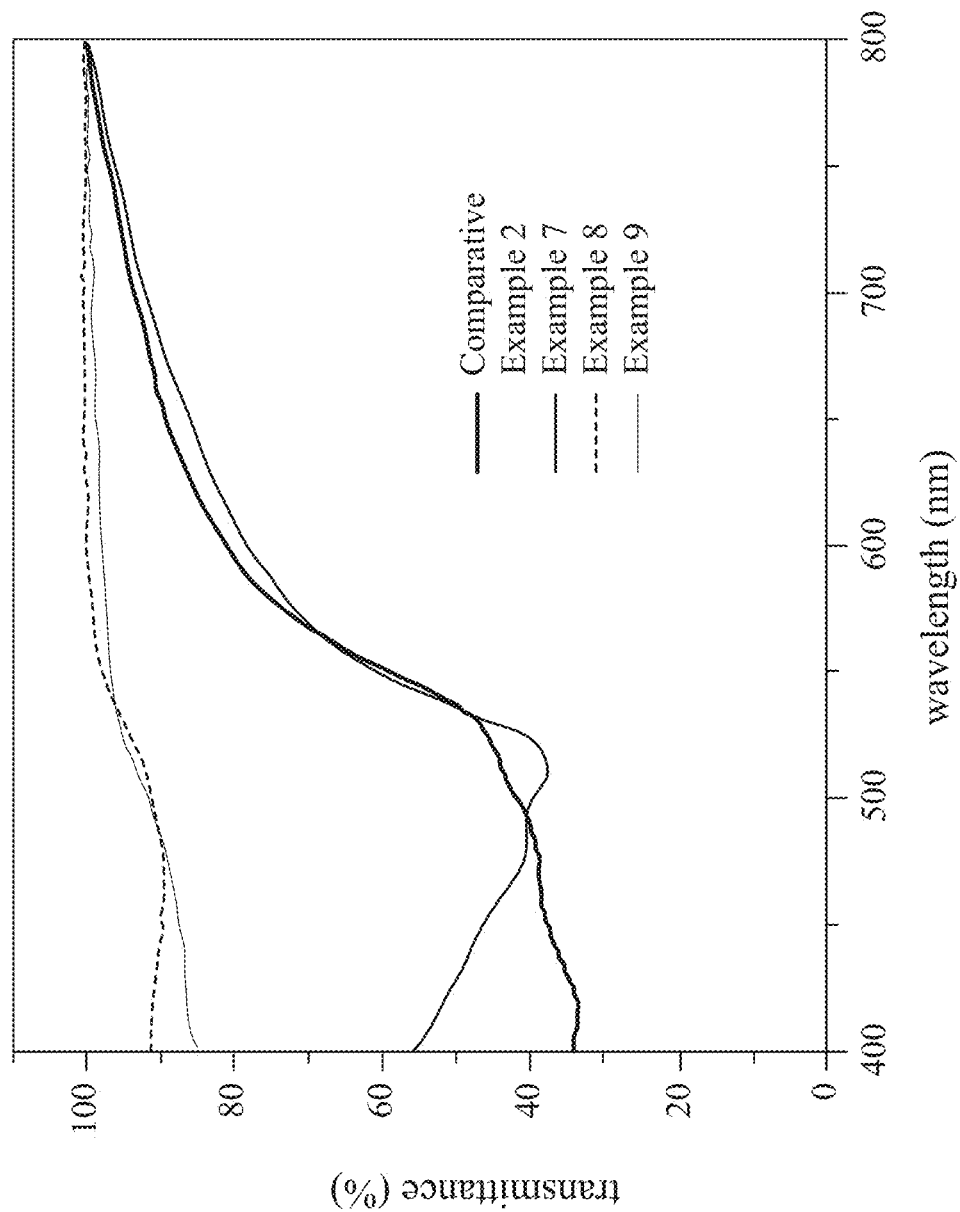
FIG. 13 is an UV-vis transmission diagram of Example 7 to Example 9 and Comparative Example 2.

Please refer to FIG. 11, FIG. 12 and FIG. 13, wherein FIG. 11 is a fluorescence microscopy (FM) image of Example 1 to Example 3 and Comparative Example 1. FIG. 12 is a contact angle image of Example 1 to Example 3 and Comparative Example 1 with water. FIG. 13 is an UV-vis transmission diagram of Example 7 to Example 9 and Comparative Example 2. As shown in FIG. 11, it can be seen that Example 1 to Example 3 and Comparative Example 1 can be aggregated into micron-scale particles, while the aggregated particles of Example 1 are larger, and the particle size can be 20 μm to 50 μm.

Furthermore, as shown in FIG. 12 and FIG. 13, it can be seen that the contact angles of Example 2 and Example 3 to water are smaller than that of Example 1, indicating that the introduction of the sulfonyl group in the side chain will increase the affinity to the water surface, so as to cause the formation of low degree of the aggregated particles. Therefore, when preparing the solution system, the light transmittance of Example 7 is lower than that of Example 8 to Example 9, which is attributed to the strong multiple scattering effect and light absorption ability to indicate that the certain degree of aggregation is beneficial to improve the photocatalytic activity.

Figure 14:
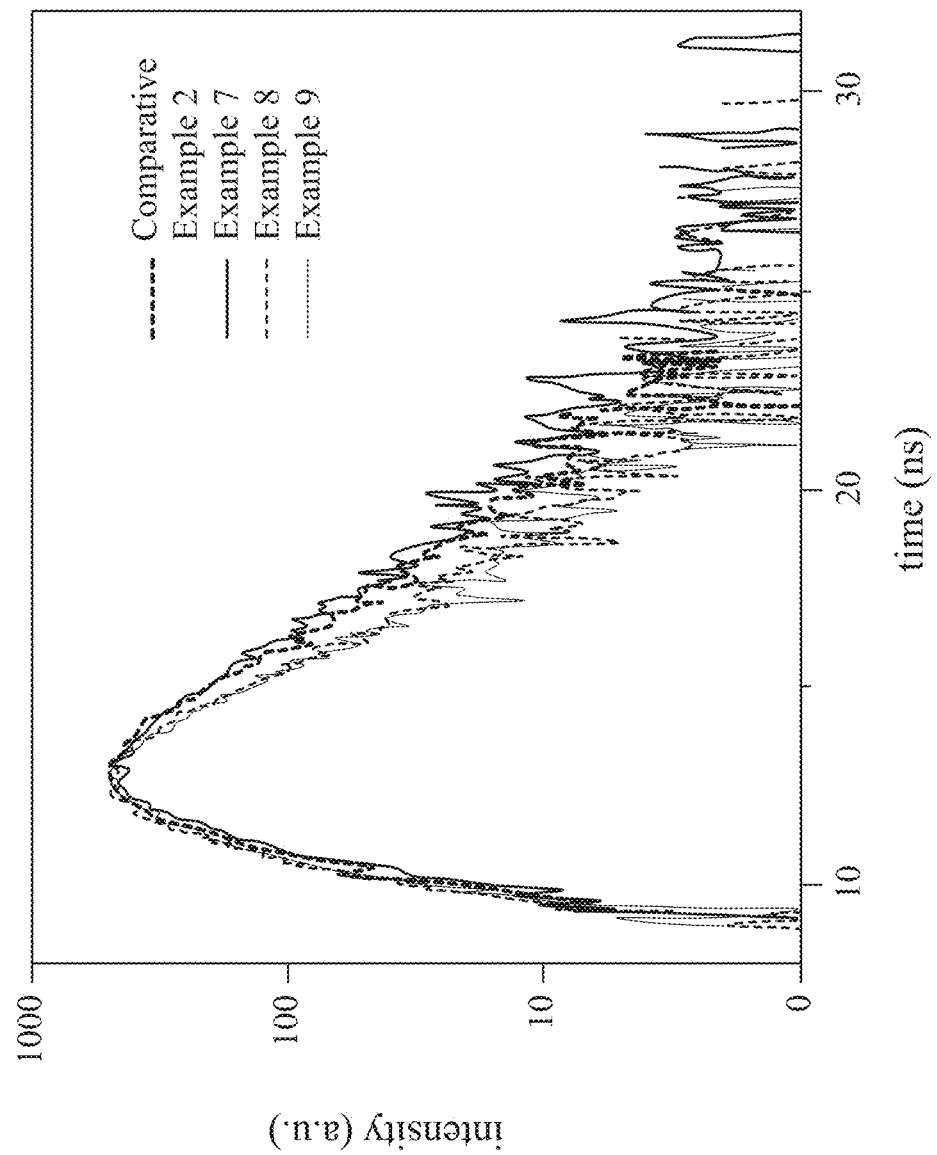
FIG. 14 is a time-resolved transient photoluminescence decay spectra of Example 7 to Example 9 and Comparative Example 2.

Please refer to FIG. 14, which is a time-resolved transient photoluminescence decay (TRPL) spectra of Example 7 to Example 9 and Comparative Example 2 to estimate the lifetime of the asymmetric fused aromatic ring derivative containing sulfonyl group, and the results are recorded in Table 12. It can be seen that Example 7 has the longest lifetime to indicate that the asymmetric fused aromatic ring derivative containing sulfonyl group of Example 1 can exhibit the slow electron hole recombination rate, which is beneficial for increasing the photocatalytic activity.

TABLE 12

|  | Example 7 | Example 8 | Example 9 | Comparative Example 2 |
|---|---|---|---|---|
| lifetime (ns) | 1.53 | 0.94 | 1.01 | 1.34 |

In conclusion, the asymmetric fused aromatic ring derivative containing sulfonyl group of the present disclosure can be a kind of asymmetric dual-acceptor type conjugated polymer, and the sulfonyl group contained in it can provide the high wettability and increase the electron-output sites, and has the better harvesting of solar energy. Therefore, when the asymmetric fused aromatic ring derivative containing sulfonyl group used as the photocatalyst in the hydrogen production device, it can produce excellent hydrogen production efficiency. More importantly, the apparent quantum yield of the asymmetric fused aromatic ring derivative containing sulfonyl group of the present disclosure at the wavelength of 500 nm breaks the current research record, so that it can be widely used in the related devices of solar energy conversion or in the field of the organic electronics.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. An asymmetric fused aromatic ring derivative containing sulfonyl group, being a repeating unit represented by the following:

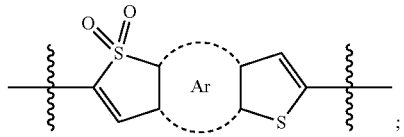

wherein each wavy lines independently indicates to connect with a monomer unit, and the monomer unit is coupling connected to the repeating unit, and Ar is a structure represented by formula (i-1):

Formula (i-1)

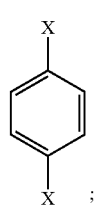

wherein each X is independently an organic ring, which is substituted or unsubstituted, or an alkyl group with linear, branched or cyclic of 1 to 30 carbon atoms.

2. The asymmetric fused aromatic ring derivative containing sulfonyl group of claim 1, wherein the organic ring is benzene, cyclopentadiene, indene, naphthalene, azulene, heptalene, indacene, acenaphthylene, fluorene, spiro-fluorene, phenalene, phenanthrene, anthracene, fluoranthene, triphenylene, pyrene, chrysene, thiophene, pyrrol, imidazole, pyrazole, triazole, thiazole, oxazole, isothiazole, isoxazole, benzothiazole, benzoimidazole, benzooxazole, pyridine, pyrazine, pyrimidine, pyridazine, isoindole, indole, indazole, purine, isoquinoline, quinoline, phthalazine, naphthyridine, quinoxaline, quinazoline, cinnoline, phenanthridine, acridine, phenanthroline or phenoxazine.

3. The asymmetric fused aromatic ring derivative containing sulfonyl group of claim 1, wherein the monomer unit is a structure represented by formula (ii-1), formula (ii-2), formula (ii-3), formula (ii-4), formula (ii-5), formula (ii-6), formula (ii-7), formula (ii-8), formula (ii-9), formula (ii-10), formula (ii-11), formula (ii-12), formula (ii-13), formula (ii-14), formula (ii-15), formula (ii-16), formula (ii-17), formula (ii-18), formula (ii-19), formula (ii-20), formula (ii-21), formula (ii-22), formula (ii-23), formula (ii-24), formula (ii-25), formula (ii-26), formula (ii-27), formula (ii-28), formula (ii-29), formula (ii-30), formula (ii-31) or formula (ii-32):

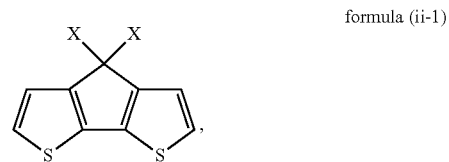

formula (ii-1)

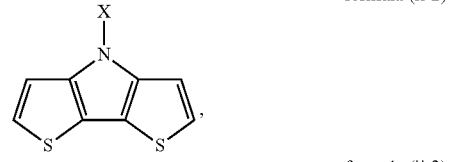

formula (ii-2)

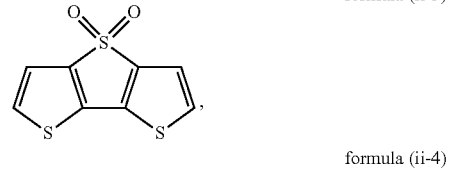

formula (ii-3)

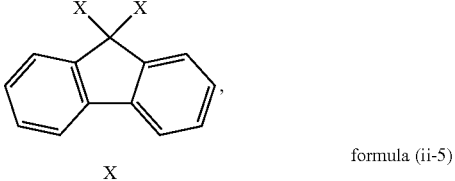

formula (ii-4)

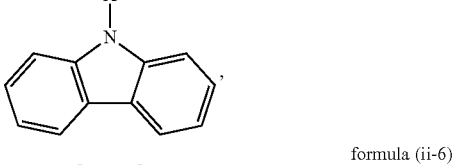

formula (ii-5)

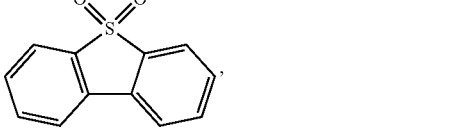

formula (ii-6)

-continued
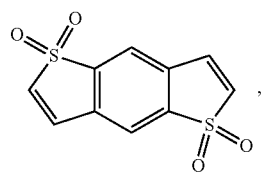
formula (ii-7)
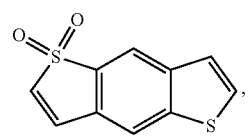
formula (ii-8)
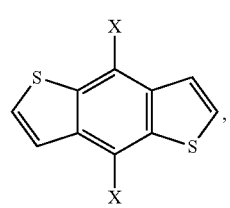
formula (ii-9)
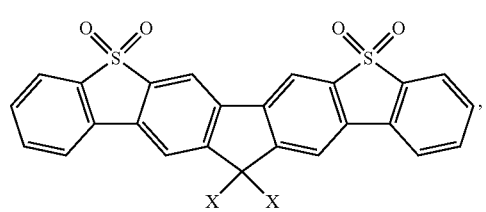
formula (ii-10)
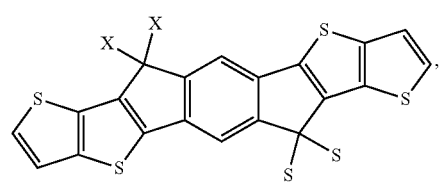
formula (ii-11)
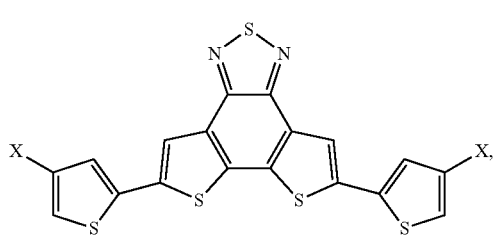
formula (ii-12)
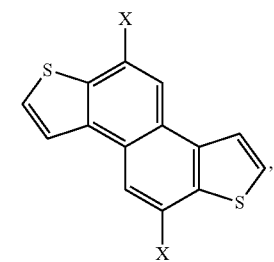
formula (ii-13)
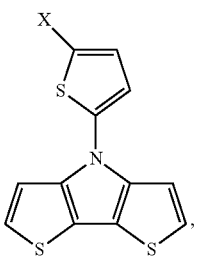
formula (ii-14)
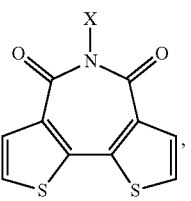
formula (ii-15)
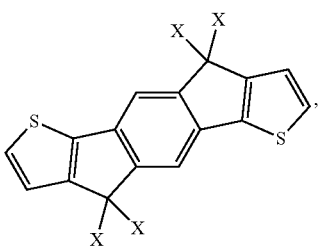
formula (ii-16)
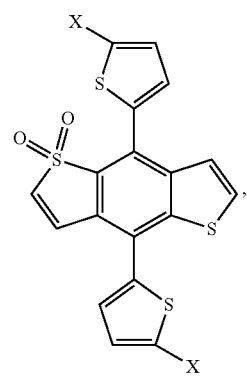
formula (ii-17)
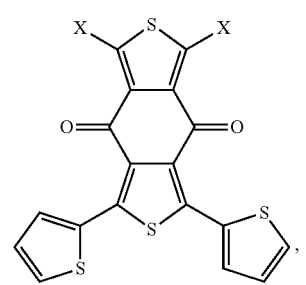
formula (ii-18)

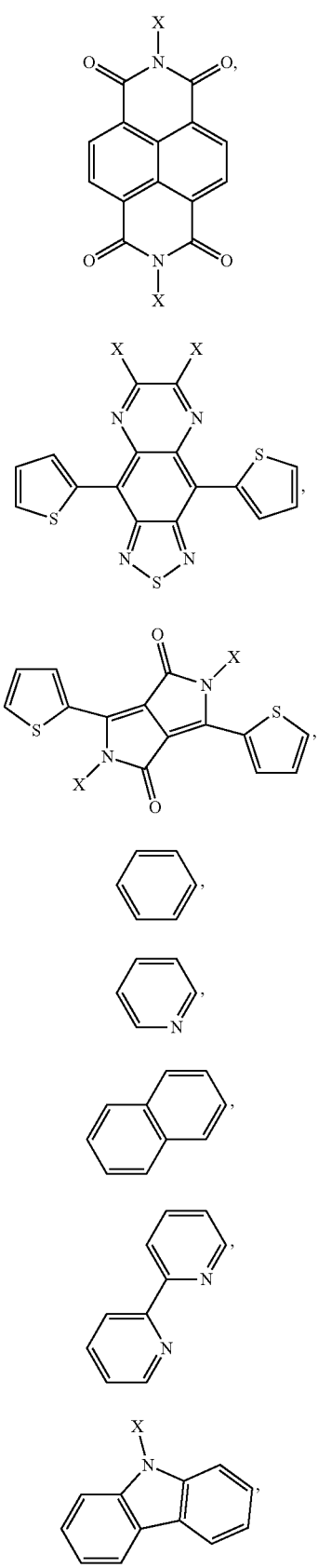

formula (ii-19)

formula (ii-20)

formula (ii-21)

formula (ii-22)

formula (ii-23)

formula (ii-24)

formula (ii-25)

formula (ii-26)

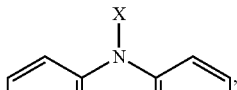 formula (ii-27)

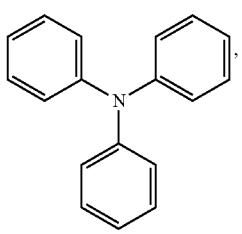 formula (ii-28)

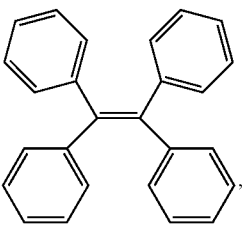 formula (ii-29)

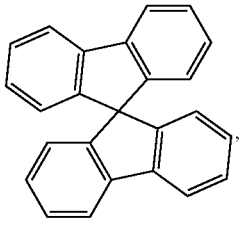 formula (ii-30)

 formula (ii-31)

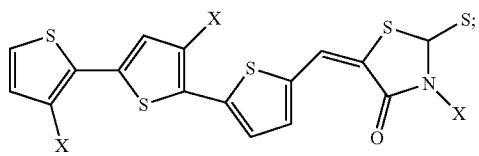 formula (ii-32)

wherein each X is independently an organic ring, which is substituted or unsubstituted, or an alkyl group with linear, branched or cyclic of 1 to 30 carbon atoms.

4. The asymmetric fused aromatic ring derivative containing sulfonyl group of claim 3, wherein the organic ring is benzene, cyclopentadiene, indene, naphthalene, azulene, heptalene, indacene, acenaphthylene, fluorene, spiro-fluorene, phenalene, phenanthrene, anthracene, fluoranthene, triphenylene, pyrene, chrysene, thiophene, pyrrol, imidazole, pyrazole, triazole, thiazole, oxazole, isothiazole, isoxazole, benzothiazole, benzoimidazole, benzooxazole, pyridine, pyrazine, pyrimidine, pyridazine, isoindole, indole, indazole, purine, isoquinoline, quinoline, phthalazine, naphthyridine, quinoxaline, quinazoline, cinnoline, phenanthridine, acridine, phenanthroline or phenoxazine.

5. The asymmetric fused aromatic ring derivative containing sulfonyl group of claim 1, wherein the asymmetric fused aromatic ring derivative containing sulfonyl group is a structure represented by formula (I-1), formula (I-2), formula (I-3), formula (I-4), formula (I-5) or formula (I-6):

formula (I-1)

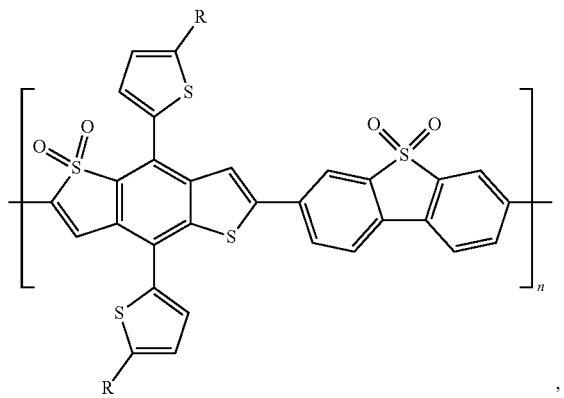

formula (I-2)

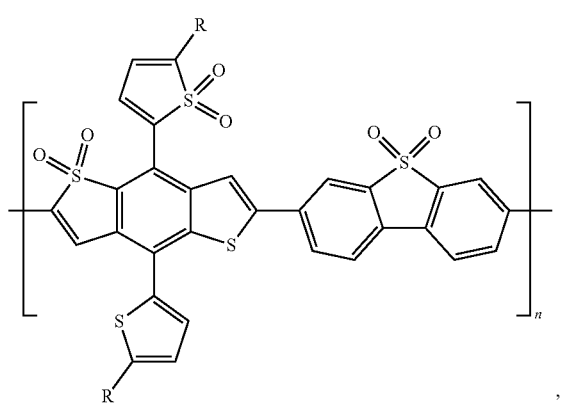

formula (I-3)

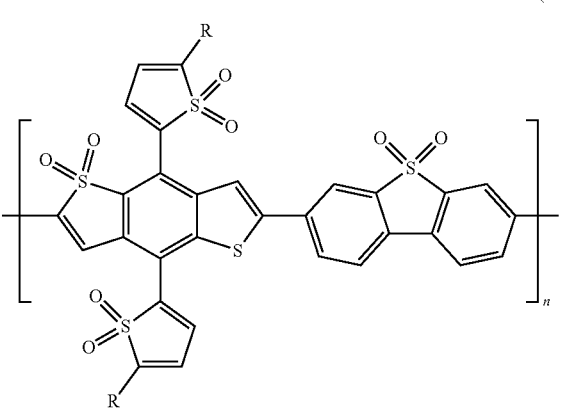

-continued formula (I-4)

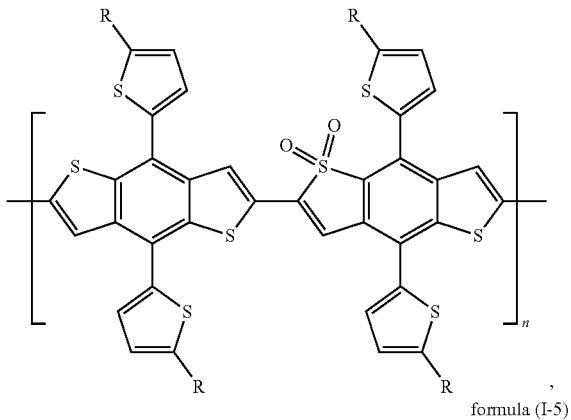

formula (I-5)

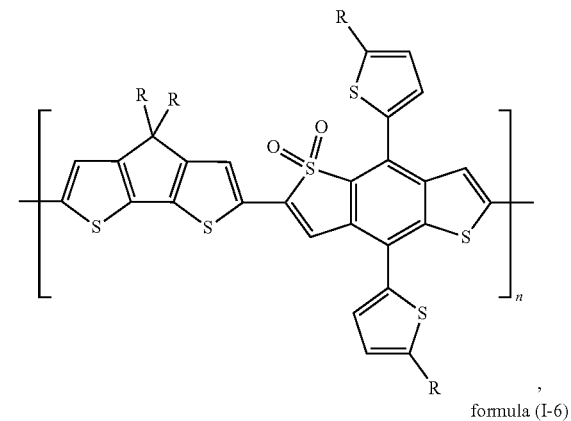

formula (I-6)

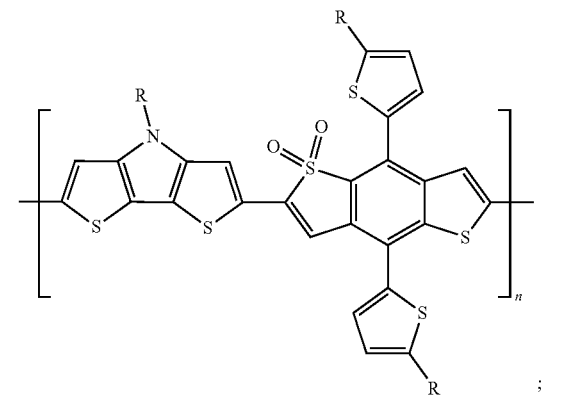

wherein R is 2-ethylhexyl, and n is an integer from 1 to 100.

6. A hydrogen production device, comprising:
a solution system, wherein the solution system comprises the asymmetric fused aromatic ring derivative containing sulfonyl group of claim 1 and water.

7. The hydrogen production device of claim 6, wherein the solution system further comprises an additive.

8. An optoelectronic component, comprising:
the asymmetric fused aromatic ring derivative containing sulfonyl group of claim 1.

9. The optoelectronic component of claim 8, wherein the optoelectronic component is an organic solar cell, an organic light-emitting diode, an organic transistor, an organic photodetector or a biological imaging.

* * * * *